United States Patent
Dean et al.

(10) Patent No.: US 6,617,137 B2
(45) Date of Patent: Sep. 9, 2003

(54) METHOD OF AMPLIFYING WHOLE GENOMES WITHOUT SUBJECTING THE GENOME TO DENATURING CONDITIONS

(75) Inventors: Frank B. Dean, Guilford, CT (US); Roger S. Lasken, New Haven, CT (US)

(73) Assignee: Molecular Staging Inc., New Haven, CT (US)

( * ) Notice: Subject to any disclaimer, the term of this patent is extended or adjusted under 35 U.S.C. 154(b) by 0 days.

(21) Appl. No.: 09/982,212

(22) Filed: Oct. 18, 2001

(65) Prior Publication Data

US 2003/0118998 A1 Jun. 26, 2003

Related U.S. Application Data

(63) Continuation of application No. 09/977,868, filed on Oct. 15, 2001.

(51) Int. Cl.$^7$ ................................................ C12P 19/34

(52) U.S. Cl. ..................................... 435/91.1; 435/91.2

(58) Field of Search ................................. 435/91.1, 91.2

(56) References Cited

U.S. PATENT DOCUMENTS

| | | | |
|---|---|---|---|
| 3,687,808 | A | 8/1972 | Merigan et al. |
| 5,001,050 | A | 3/1991 | Blanco et al. |
| 5,043,272 | A | 8/1991 | Hartley |
| 5,198,543 | A | 3/1993 | Blanco et al. |
| 5,539,082 | A | 7/1996 | Nielsen et al. |
| 5,563,037 | A | 10/1996 | Sutherland et al. |
| 5,714,331 | A | 2/1998 | Buchardt et al. |
| 5,719,262 | A | 2/1998 | Buchardt et al. |
| 5,854,033 | A | 12/1998 | Lizardi |
| 6,033,881 | A | * 3/2000 | Himmler et al. ............ 435/91.2 |
| 6,124,120 | A | 9/2000 | Lizardi |
| 6,143,495 | A | 11/2000 | Lizardi et al. |
| 6,183,960 | B1 | 2/2001 | Lizardi |
| 6,210,884 | B1 | 4/2001 | Lizardi |
| 6,214,587 | B1 | 4/2001 | Dattagupta et al. |
| 6,255,082 | B1 | * 7/2001 | Lizardi ..................... 435/91.1 |
| 6,280,949 | B1 | 8/2001 | Lizardi |
| 6,287,768 | B1 | 9/2001 | Chenchik et al. |
| 6,287,776 | B1 | 9/2001 | Hefti |
| 6,288,220 | B1 | 9/2001 | Kambara et al. |
| 6,291,193 | B1 | 9/2001 | Kamabara et al. |
| 6,291,669 | B1 | 9/2001 | Kwiatkowski et al. |
| 6,294,664 | B1 | 9/2001 | Ravikumar et al. |
| 6,297,006 | B1 | 10/2001 | Drmanac et al. |
| 6,329,150 | B1 | 12/2001 | Lizardi et al. |
| 6,344,329 | B1 | 2/2002 | Lizardi |

FOREIGN PATENT DOCUMENTS

| | | |
|---|---|---|
| EP | 0 070 685 B1 | 7/1982 |
| WO | WO 97/17076 | 5/1997 |
| WO | WO 97/17471 | 5/1997 |

OTHER PUBLICATIONS

Aliotta et al., Thermostable Bst DNA polymerase I lacks a 3'→5' proofreading exonuclease activity. *Genet Anal.* (*Netherlands*) 12:185–195 (1996).

Beaucage et al., Deoxynucleoside Phorsphoranidites—A New Class of Key Intermediates For Deoxypolynucleotide Synthesis. *Tetrahedron Lett.* 22:1859–1862 (1981).

Birkenmeyer et al. DNA Probe Amplification Methods. *J. Virol. Meth.* 35:117–126 (1991).

Bianco et al., Highly Efficient DNA Synthesis by the Phage φ29 DNA Polymerase.*J. Biol. Chem.* 264:8935–8940 (1989).

Boehmer et al., Herpes Simplex Virus Type 1 ICP8: Helix–Destabilizing Properties . . . *J. Virol.* 67(2):711–715 (1993).

Buchanan et al., Long DOP–PCR of Rare Archival Anthropological Samples, *Hum. Biol.* 72:911–925 (2000).

Chatterjee et al., Cloning and Overexpression of the Gene Encoding Bateriophage T5 DNA Polymerase. *Gene* 97:13–19 (1991).

Cheung et al., Whole genome amplification using a degenerate oligonucleotide primer allows hundreds of genotypes to be performed on less than one nanogram of genomic DNA, *Proc Natl Acad Sci USA* 93:14676–14679 (1996).

Crooke et al., Antisense Research and Applications. *CRC Press* 16:290–301 (1993).

Eckert et al., DNA Polymerase Fidelity and the Polymerase Chain Reaction, *PCR Methods and Applications* 1:17–24 (1991).

Englisch et al., Chemically Modified Oligonucleotides as Probes and Inhibitors. *Angewandte Chemie,* International Edition in English 30(6):613–629 (1991).

Esteban et al., Fidelity of φ29 DNA Polymerase. Comparison between Protein—Protein Initiation and DNA Polymerization, *J. Biol. Chem.* , 268:2719–2726 (1993).

(List continued on next page.)

*Primary Examiner*—Kenneth R. Horlick
(74) *Attorney, Agent, or Firm*—Needle & Rosenberg, P.C.

(57) ABSTRACT

Disclosed are compositions and a method for amplification of nucleic acid sequences of interest. The disclosed method generally involves replication of a target sequence such that, during replication, the replicated strands are displaced from the target sequence by strand displacement replication of another replicated strand. In one form of the disclosed method, the target sample is not subjected to denaturing conditions. It was discovered that the target nucleic acids, genomic DNA, for example, need not be denatured for efficient multiple displacement amplification. The primers used can be hexamer primers. The primers can also each contain at least one modified nucleotide such that the primers are nuclease resistant. The primers can also each contain at least one modified nucleotide such that the melting temperature of the primer is altered relative to a primer of the same sequence without the modified nucleotide(s). The DNA polymerase can be φ29 DNA polymerase.

6 Claims, 11 Drawing Sheets

OTHER PUBLICATIONS

Faruqi et al., High–Throughput Genotyping of Single Nucleotide Polymorphisms with Rolling Circle Amplication, *BMC Genomics* 2:4 (2001).

Gillespie et al., HLA class II typing of whole genome amplified mouth swab DNA, *Tissue Antigens* 56:530–538 (2000).

Guillier–Gencik et al., Generation of whole–chromosome painting probes specific to each chicken macrochromosome, *Cytogenet Cell Genet.* 87:282–285 (1999).

Guo et al., Direct Fluorescence Analysis of Genetic Polymorphisms by Hybridization with Oligonucleotide Arrays on Glass Supports, *Nucl. Acids Res.* 22(24):5456–5465 (1994).

Hall et al., Mixed Anhydrides as Intermediates in the Synthesis of Dinucleoside Phosphates. *J. Chem. Soc.* 3291–3296 (1957).

Harper et al., Recent Advances and Future Developments in PGD, *Prenat. Diagn.* 19:1193–1199 (1999).

Henegariu et al., Custom fluorescent–nucleotide synthesis as an alternative method for nucleic acid labeling. *Nature Biotechnology* 18:345–348 (2000).

Hoy et al., Bromodeoxyuridine/DNA Analysis of Replication in CHO Cells after Exposure to UV Light, *Mutat. Res.* 290:217–230 (1993).

Itakura et al., Synthesis and Use of Synthetic Oligonucleotides. *Ann. Rev. Biochem.* 53:323–356 (1984).

Iyer et al., 3H–1, 2–Benzodithiole–3–one 1, 1–Dioxide as am Improved Sulfurizing Reagent in the Solid–Phase Synthesis of Oligodeoxyribonucleotides Phosphorothioates. *J. Am. Chem. Soc.* 112:1253–1254 (1990).

Jacobsen et al., The N–Terminal Amino–Acid Sequences of DNA Polymerase I from *Escherichis coli* and of the Large and the Small Fragments Obtained by a Limited Proteolysis. *Eur. J. Biochem.* 45:623–627 (1974).

Jung et al., Bacteriophage PRD1 DNA polymerases: Evolution of DNA polymerases. *Proc. Natl. Acad. Sci. USA* 84:8287–8291 (1987).

Kaboord et al., Accessory proteins function as matchmakers in the assembly of the T4 DNA polymerase holoenzyme. *Curr. Biol.* 5(2):149–157 (1995).

Kerkhof, A Comparison of Substrates for Quantifying the Signal from a Nonradiolabeled DNA Probe, *Anal. Biochem.* 205:359–364 (1992).

Khrapko et al., Hybridization of DNA with Oligonucleotides Immobilized in Gel: A Convenient Method for Detecting Single Base Substitutions. *Mol Biol (Mosk) (USSR)* 581–591 (1991).

Kim et al., Whole genome amplification and molecular genetic analysis of DNA from paraffin–embedded prostate adenocarcinoma tumor tissue, *J. Urol.* 162:1512–1518 (1999).

Klein et al., Comparative genomic hybridization, loss of heterozygosity, and DNA sequence analysis of single cells, *Proc Natl Acad Sci* USA 96:4494–4499 (1999).

King, et al., Characterization of a DNA Polymerase from the Hypertheromphile Archaea, *Thermococcus litoralis*. *J. Biol. Chem.* 1268(3):1965–1975 (1993).

Kukasjaarvi et al., Optimizing DOP–PCR for Universal Amplification of Small DNA Samples in Comparative Genomic Hybridization. *Genes, Chromosomes and Cancer* 18:94–101 (1997).

Landegren, Molecular mechanics of nucleic acid sequence amplification, *Trends Genetics* 9:199–202 (1993).

Langer et al., Enzymatic synthesis of biotin–labeled polynucleotides: Novel nucleic acid affinity probes, *Proc. Natl. Acad. Sci. USA* 78(11):6633–6637 (1981).

Lantz et al., Biotechnical use of polymerase chain reaction for microbiological analysis of biological samples. *Biotechnol. Annu. Rev.* 5:87–130 (2000).

Lesnick et al., Relative Thermodynamic Stability of DNA, RNA, and DNA: RNA Hybrid Duplexes: Relationship with Base Composition and Structure *Biochemistry* 34:10807–10815 (1995).

Letsinger et al., Synthesis of Thymidine Oligonucleotides by Phosphite Triester Inteermediates. *J. Am. Chem. Soc.* 9:3655 (1976).

Lockhart et al., Expression monitoring by hybridization to high–density oligonucleotide arrays. *Nature Biotechnology* 14:1675–1680 (1996).

Matsumoto et al., Primary structure of bacteriphage M2 DNA polymerase: conserved segments within protein–priming DNA polymerase and DNA polymerase I of *Escherichia coli*. *Gene* 84:247–255 (1989).

Matteucci et al., Synthesis of Deoxyoligonucleotides on a Polymer Support. *J. Am. Chem. Soc.* 103:3185 (1981).

McGraw et al., Sequence–Dependent Oligonucleotide–Target Duplex Stabilities: Rule from empirical Studies with a Set of Twenty–Mers. *Biotechniques* 8:674–678 (1990).

Narang et al., Chemical Synthesis of Deoxioligonucleotides by the Modified Triester Method. *Meth. Enzymol.* 65:610–620 (1980).

Nielsen et al., Peptide Nucleic Acid (PNA). A DNA Mimic with a Peptide Backbone. *Bioconjug. Chem.* 5:3–7 (1994).

Nielsen et al., Sequence–Selective Recognition of DNA by Strand Displacement with a Thymine–Substituted Polymide. *Science* 254:1497–1500 (1991).

Paulson et al., Loss of Heterozygosity Analysis Using Whole Genome Amplification, Cell sorting, and Fluorescence–Based PCR, *Genome Res.* 9:482–491 (1999).

Paunio et al., Preimplantation diagnosis by whole–genome amplification, PCR amplification, and solid–phase minisequencing of blastomere. *Clin. Chem.* 42:1382–1390 (1994).

Pease et al., Light–Generated Oligonucleotide Arrays for Rapid DNA Sequence Analysis. *Proc. Natl. Acad. Sci. USA,* 91(11):5022–5026 (1994).

Pless et al., Solid support synthesis of oligothymidylates using phosphorochloridates and 1–alkylimidazoles. *Nucl. Acids Res.* 2:773 (1975).

Pruckler et al., Comparison of *Legionella pneumophila* isolates by Arbitrarily Primed PCR and Pulsed–Field Gel Electrophoresis: Analysis from Seven Epidemic Investigations. *J. Clin. Microbiol.* 33:2872–2875 (1995).

Rigler et al., Differences in the Mechanism of Stimulation of T7 DNA Polymerase by Two Binding Modes of *Escherichia coli* Single–stranded DNA–binding Protein. *J. Biol. Chem* 270(15):8910–8919 (1995).

Rychlik et al., Optimization of the Annealing Temperature for DNA Amplification in vitro. *Nucl. Acids Res.* 18(21):6409–6412 (1990).

Saiki et al., Primer–directed enzymatic amplification of DNA with a thermostable DNA polymerase, *Science* 239:487–491 (1988).

Sambrook et al., *Molecular Cloning: A Laboratory Manual,* $2^{nd}$ Edition (Cold Spring Harbor Laboratory Press, Cold Spring Harbor, NY) Chapters 5, 6 (1989).

Sanghvi. Chapter 15, Heterocyclic Base Modifications in Nucleic Acids and Their Applications in Antisense Oligonucleotides, *Antisense Res.* and Appl. p. 273–301 (1993).

Sano et al., Detection of heavy methylation in human repetitive DNA subsets by a monoclonal antibody against 5–methylcytosine. *Biochim. Biophys. Acta* 951:157–165 (1988).

Schena et al., Quantitative Monitoring of Gene Expression Patterns with a Complementary DNA Microarray. *Science* 270:487–470 (1995).

Siegel et al., A Novel DNA Helicase from Calf Thymus. *J. Biol. Chem.* 267(19):13629–13635 (1992).

Skaliter et al., Rolling Circle DNA Replication in vitro by a complex of Herpes Simplex Virus Type 1–encoded Enzymes. *Proc. Natl. Acad. Sci. USA* 91(22):10665–10669 (1994).

Southern, Detection of specific sequences among DNA fragments separated by gel electrophoresis, *J. Mol. Biol.* 98:503–517 (1975).

Stimpson et al., Real–Time Detection of DNA Hybridization and Melting on Oligonucleotide Arrays by Using Optical Wave Guides, *Proc Natl. Acad. Sci. USA*, 92(14):6379–6383 (1995).

Telenius et al., Degenerate Oligonucleotide–Primed PCR: General Amplification of Target DNA by a Single Degenerate Primer. *Genomics* 13:718–725 (1992).

Tenover et al., Comparison of Traditional and Molecular Methods of Typing Isolates of *Staphylococcus aureus*. *J. Clin. Microbiol.* 32:407–415 (1994).

Tsurumi et al., Functional Interaction between Epstein–Barr Virus DNA Polymerase Catalytic Subunit and Its Accessory Subunit In Vitro. *J. Virol.* 67(12):7648–7653 (1993).

Tyagi et al., Molecular Beacons: Probes that Fluoresce Upon Hybridization. *Nat. Biotech.*, 14(3):303–308 (1996).

Villemain et al., The N–Terminal B–Domain of T4 Gene 32 Protein Modulates the Lifetime of Cooperatively Bound Gp32–ss Nucleic Acid Complexes. *Biochemistry* 35:14395–14404 (1996).

Walker et al., Detection of *Mycobacterium tuberculosis* DNA with thermophilic strand displacement amplification and fluorescence polarization. *Clinical Chemistry* 42(10):1604–1608 (1996).

Wansick et al., Fluorescent Labeling of Nascent RNA Reveals Transcription by RNA Polymerase II in Domains Scattered Throughout the Nucleus. *J. of Cell Biol.* 122(2):283–293 (1993).

Wells et al., Detailed chromosomal and molecular genetic analysis of single cells by whole genome amplification and comparative genomic hybridization, *Nucl. Acids Res.* 27:1214–1218 (1999).

Wells et al., Comprehensive chromosomal analysis of human preimplantation embryos using whole genome amplification and single cell comparative genomic hybridization, *Mol. Hum. Reprod.* 6:1055–1062 (2000).

Yu et al., Cyanine dye dUTP analogs for enzymatic labeling of DNA probes, *Nucl. Acids Res.*, 22(15):3226–3232 (1994).

Zhang et al., Whole genome amplification from a single cell: implications for genetic analysis, *Proc Natl Acad Sci USA* 89:5847–5851 (1992).

Zhu et al., Purification and characterization of PRD1 DNA polymerase. *Biochim. Biophys. Acta* 1219:267–276 (1994).

Zijderveld et al., Helix–Destabilizing Properties of the Adenovirus DNA–Binding Protein. *J. Virol.* 68(2):1158–1164 (1994).

* cited by examiner

Amplification of c-jun sequence using Gene Specific MDA

Specific amplification of c-jun sequences from human genomic DNA

METHOD OF AMPLIFYING WHOLE GENOMES WITHOUT SUBJECTING THE GENOME TO DENATURING CONDITIONS

This application is a continuation of the copending application Ser. No. 09/977,868, filed Oct. 15, 2001, entitled "Nucleic Acid Amplification," by Frank B. Dean, Roger S. Lasken, Linhua Fang, A. Fawad Faruqi, Osama A. Alsmadi, Mark D. Driscoll, and Seiyu Hosono. Application Ser. No. 09/977,868, filed Oct. 15, 2001, entitled "Nucleic Acid Amplification," by Frank B. Dean, Roger S. Lasken, Linhua Fang, A. Fawad Faruqi, Osama A. Alsmadi, Mark D. Driscoll, and Seiyu Hosono, is hereby incorporated herein by reference in its entirety.

FIELD OF THE INVENTION

The disclosed invention is generally in the field of nucleic acid amplification.

BACKGROUND OF THE INVENTION

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics* 9:199–202 (1993)).

Fundamental to most genetic analysis is availability of genomic DNA of adequate quality and quantity. Since DNA yield from human samples is frequently limiting, much effort has been invested in general methods for propagating and archiving genomic DNA. Methods include the creation of EBV-transformed cell lines or whole genome amplification (WGA) by random or degenerate oligonucleotide-primed PCR. Whole genome PCR, a variant of PCR amplification, involves the use of random or partially random primers to amplify the entire genome of an organism in the same PCR reaction. This technique relies on having a sufficient number of primers of random or partially random sequence such that pairs of primers will hybridize throughout the genomic DNA at moderate intervals. Replication initiated at the primers can then result in replicated strands overlapping sites where another primer can hybridize. By subjecting the genomic sample to multiple amplification cycles, the genomic sequences will be amplified. Whole genome PCR has the same disadvantages as other forms of PCR. However, WGA methods suffer from high cost or insufficient coverage and inadequate average DNA size (Telenius et al., *Genomics*. 13:718–725 (1992); Cheung and Nelson, *Proc Natl Acad Sci USA*. 93:14676–14679 (1996); Zhang et al., *Proc Natl Acad Sci USA*. 89:5847–5851 (1992)).

Another field in which amplification is relevant is RNA expression profiling, where the objective is to determine the relative concentration of many different molecular species of RNA in a biological sample. Some of the RNAs of interest are present in relatively low concentrations, and it is desirable to amplify them prior to analysis. It is not possible to use the polymerase chain reaction to amplify them because the mRNA mixture is complex, typically consisting of 5,000 to 20,000 different molecular species. The polymerase chain reaction has the disadvantage that different molecular species will be amplified at different rates, distorting the relative concentrations of mRNAs.

Some procedures have been described that permit moderate amplification of all RNAs in a sample simultaneously. For example, in Lockhart et al., *Nature Biotechnology* 14:1675–1680 (1996), double-stranded cDNA was synthesized in such a manner that a strong RNA polymerase promoter was incorporated at the end of each cDNA. This promoter sequence was then used to transcribe the cDNAs, generating approximately 100 to 150 RNA copies for each cDNA molecule. This weak amplification system allowed RNA profiling of biological samples that contained a minimum of 100,000 cells. However, there is a need for a more powerful amplification method that would permit the profiling analysis of samples containing a very small number of cells.

Another form of nucleic acid amplification, involving strand displacement, has been described in U.S. Pat. No. 6,124,120 to Lizardi. In one form of the method, two sets of primers are used that are complementary to opposite strands of nucleotide sequences flanking a target sequence. Amplification proceeds by replication initiated at each primer and continuing through the target nucleic acid sequence, with the growing strands encountering and displacing previously replicated strands. In another form of the method a random set of primers is used to randomly prime a sample of genomic nucleic acid. The primers in the set are collectively, and randomly, complementary to nucleic acid sequences distributed throughout nucleic acid in the sample. Amplification proceeds by replication initiating at each primer and continuing so that the growing strands encounter and displace adjacent replicated strands. In another form of the method concatenated DNA is amplified by strand displacement synthesis with either a random set of primers or primers complementary to linker sequences between the concatenated DNA. Synthesis proceeds from the linkers, through a section of the concatenated DNA to the next linker, and continues beyond, with the growing strands encountering and displacing previously replicated strands.

BRIEF SUMMARY OF THE INVENTION

Disclosed are compositions and a method for amplification of nucleic acid sequences of interest. The method is based on strand displacement replication of the nucleic acid sequences by multiple primers. The disclosed method, referred to as multiple displacement amplification (MDA), improves on prior methods of strand displacement replication. The disclosed method generally involves bringing into contact a set of primers, DNA polymerase, and a target sample, and incubating the target sample under conditions that promote replication of the target sequence. Replication of the target sequence results in replicated strands such that, during replication, the replicated strands are displaced from the target sequence by strand displacement replication of another replicated strand.

In one embodiment of the disclosed method, the target sample is not subjected to denaturing conditions. It was discovered that the target nucleic acids, genomic DNA, for example, need not be denatured for efficient multiple displacement amplification. It was discovered that elimination of a denaturation step and denaturation conditions has additional advantages such as reducing sequence bias in the amplified products. In another embodiment, the primers can be hexamer primers. It was discovered that such short, 6 nucleotide primers can still prime multiple strand displacement replication efficiently. Such short primers are easier to produce as a complete set of primers of random sequence (random primers) than longer primers because there are fewer separate species of primers in a pool of shorter primers. In another embodiment, the primers can each contain at least one modified nucleotide such that the primers are nuclease resistant. In another embodiment, the primers can each contain at least one modified nucleotide such that the melting temperature of the primer is altered relative to a primer of the same sequence without the modified nucleotide(s). For these last two embodiments, it is preferred that the primers are modified RNA. In another embodiment, the DNA polymerase can be φ29 DNA polymerase. It was discovered that φ29 DNA polymerase produces greater amplification in multiple displacement amplification. The combination of two or more of the above features also yields improved results in multiple displacement amplification. In a preferred embodiment, for example, the target sample is not subjected to denaturing conditions, the primers are hexamer primers and contain modified nucleotides such that the primers are nuclease resistant, and the DNA polymerase is φ29 DNA polymerase. The above features are especially useful in whole genome strand displacement amplification (WGSDA).

In another embodiment of the disclosed method, the method includes labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, bromodeoxyuridine triphosphate (BrdUTP), or 5-(3-aminoallyl)-2'-deoxyuridine 5'-triphosphates, to the 3' ends of the replicated strands. The replicated strands can also be labeled by incorporating modified nucleotides during replication. Probes replicated in this manner are particularly useful for hybridization, including use in microarray formats.

In one form of the disclosed method, referred to as whole genome strand displacement amplification (WGSDA), a random set of primers is used to randomly prime a sample of genomic nucleic acid (or another sample of nucleic acid of high complexity). By choosing a sufficiently large set of primers of random or partially random sequence, the primers in the set will be collectively, and randomly, complementary to nucleic acid sequences distributed throughout nucleic acid in the sample. Amplification proceeds by replication with a highly processive polymerase initiating at each primer and continuing until spontaneous termination. A key feature of this method is the displacement of intervening primers during replication by the polymerase. In this way, multiple overlapping copies of the entire genome can be synthesized in a short time. The method has advantages over the polymerase chain reaction since it can be carried out under isothermal conditions. Other advantages of whole genome strand displacement amplification include a higher level of amplification than whole genome PCR (up to five times higher), amplification is less sequence-dependent than PCR, and there are no re-annealing artifacts or gene shuffling artifacts as can occur with PCR (since there are no cycles of denaturation and re-annealing). In preferred embodiments of WGSDA, the target sample is not subjected to denaturing conditions, the primers are hexamer primers and contain modified nucleotides such that the primers are nuclease resistant, the DNA polymerase is φ29 DNA polymerase, or any combination of these features.

In another form of the method, referred to as multiple strand displacement amplification (MSDA), two sets of primers are used, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The 5' end of primers in both sets are distal to the nucleic acid sequence of interest when the primers are hybridized to the flanking sequences in the nucleic acid molecule. Preferably, each member of each set has a portion complementary to a separate and non-overlapping nucleotide sequence flanking the target nucleotide sequence. Amplification proceeds by replication initiated at each primer and continuing through the target nucleic acid sequence. In another form of MSDA, referred to as linear MSDA, amplification is performed with a set of primers complementary to only one strand, thus amplifying only one of the strands.

In another form of the method, referred to as gene specific strand displacement amplification (GS-MSDA), target DNA is first digested with a restriction endonuclease. The digested fragments are then ligated end-to-end to form DNA circles. These circles can be monomers or concatemers. Two sets of primers are used for amplification, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The primers are designed to cover all or part of the sequence needed to be amplified. Preferably, each member of each set has a portion complementary to a separate and non-overlapping nucleotide sequence flanking the target nucleotide sequence. Amplification proceeds by replication initiated at each primer and continuing through the target nucleic acid sequence. In one form of GS-MSDA, referred to as linear GS-MSDA, amplification is performed with a set of primers complementary to only one strand, thus amplifying only one of the strands. In another form of GS-MSDA, cDNA sequences can be circularized to form single stranded DNA circles. Amplification is then performed with a set of primers complementary to the single-stranded circular cDNA.

A key feature of this method is the displacement of intervening primers during replication. Once the nucleic acid strands elongated from the right set of primers reaches the region of the nucleic acid molecule to which the left set of primers hybridizes, and vice versa, another round of priming and replication will take place. This allows multiple copies of a nested set of the target nucleic acid sequence to be synthesized in a short period of time. By using a sufficient number of primers in the right and left sets, only a few rounds of replication are required to produce hundreds of thousands of copies of the nucleic acid sequence of interest. The disclosed method has advantages over the polymerase chain reaction since it can be carried out under isothermal conditions. No thermal cycling is needed because the polymerase at the head of an elongating strand (or a compatible strand-displacement protein) will displace, and thereby make available for hybridization, the strand ahead of it. Other advantages of multiple strand displacement amplification include the ability to amplify very long nucleic acid segments (on the order of 50 kilobases) and rapid amplification of shorter segments (10 kilobases or less). In multiple strand displacement amplification, single priming events at unintended sites will not lead to artifactual amplification at these sites (since amplification at the intended site will quickly outstrip the single strand replication at the unintended site). In preferred embodiments of MSDA, the target sample is not subjected to denaturing conditions, the primers are hexamer primers and contain modified nucleotides such that the primers are nuclease resistant, the DNA polymerase is φ29 DNA polymerase, or any combination of these features.

In preferred embodiments of WGSDA, the target sample is not subjected to denaturing conditions, the primers are hexamer primers and contain modified nucleotides such that the primers are nuclease resistant, the DNA polymerase is φ29 DNA polymerase, or any combination of these features.

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A preferred form of labeling involves labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

In the disclosed method amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the whole genome strand displacement method.

Genetic analysis must frequently be carried out with DNA derived from biological samples, such as blood, tissue culture cells, buccal swabs, mouthwash, stool, tissues slices, biopsy aspiration, and archeological samples such as bone or mummified tissue. In some cases, the samples are too small to extract a sufficient amount of pure DNA and it is necessary to carry out DNA-based assays directly from the unprocessed sample. Furthermore, it is time consuming to isolate pure DNA, and so the disclosed method, which can amplify the genome directly from biological samples, represents a substantial improvement.

The disclosed method has several distinct advantages over current methodologies. The genome can be amplified directly from whole blood or cultured cells with simple cell lysis techniques such as KOH treatment. PCR and other DNA amplification methods are severely inhibited by cellular contents and so purification of DNA is needed prior to amplification and assay. For example, heme present in lysed blood cells inhibits PCR. In contrast, the disclosed form of whole genome amplification can be carried out on crude lysates with no need to physically separate DNA by miniprep extraction and precipitation procedures, or with column or spin cartridge methods.

Bacteria, fungi, and viruses may all be involved in nosocomial infections. Identification of nosocomial pathogens at the sub-species level requires sophisticated discriminatory techniques. Such techniques utilize traditional as well as molecular methods for typing. Some traditional techniques are antimicrobial susceptibility testing, determination of the ability to utilize biochemical substrates, and serotyping. A major limitation of these techniques is that they take several days to complete, since they require pure bacterial cultures. Because such techniques are long, and the bacteria may even be non-viable in the clinical samples, there is a need to have a quick and reliable method for bacterial species identification.

Some of the DNA-based molecular methods for the identification of bacterial species are macrorestriction analysis (MRA) followed by pulsed-field gel electrophoresis (PFGE), amplified fragment length polymorphism (AFLP) analysis, and arbitrarily primed PCR (AP-PCR) (Tenover et al., J. Clin. Microbiol. 32:407–415 (1994), and Pruckler et al., J. Clin. Microbiol. 33:2872–2875 (1995)). These molecular techniques are labor-intensive and difficult to standardize among different laboratories.

The disclosed method provides a useful alternative method for the identification of bacterial strains by amplification of microbial DNA for analysis. Unlike PCR (Lantz et al., Biotechnol. Annu. Rev. 5:87–130 (2000)), the disclosed method is rapid, non-biased, reproducible, and capable of amplifying large DNA segments from bacterial, viral or fungal genomes.

The disclosed method can be used, for example, to obtain enough DNA from unculturable organisms for sequencing or other studies. Most microorganisms cannot be propagated outside their native environment, and therefore their nucleic acids cannot be sequenced. Many unculturable organisms live under extreme conditions, which makes their genetic complement of interest to investigators. Other microorganisms live in communities that play a vital role in certain ecosystems. Individual organisms or entire communities of organisms can be amplified and sequenced, individually or together.

Recombinant proteins may be purified from a large biomass grown up from bacterial or yeast strains harboring desired expression vectors. A high degree of purity may be desired for the isolated recombinant protein, requiring a sensitive procedure for the detection of trace levels of protein or DNA contaminants. The disclosed method is a DNA amplification reaction that is highly robust even in the presence of low levels of DNA template, and can be used to monitor preparations of recombinant protein for trace amounts of contaminating bacterial or yeast genomic DNA.

Amplification of forensic material for RFLP-based testing is one useful application for the disclosed method.

It is an object of the disclosed invention to provide a method of amplifying a target nucleic acid sequence in a continuous, isothermal reaction.

It is another object of the disclosed invention to provide a method of amplifying an entire genome or other highly complex nucleic acid sample in a continuous, isothermal reaction.

It is another object of the disclosed invention to provide a method of amplifying a target nucleic acid sequence where multiple copies of the target nucleic acid sequence are produced in a single amplification cycle.

It is another object of the disclosed invention to provide a method of amplifying a concatenated DNA in a continuous, isothermal reaction.

It is another object of the disclosed invention to provide a kit for amplifying a target nucleic acid sequence in a continuous, isothermal reaction.

It is another object of the disclosed invention to provide a kit for amplifying an entire genome or other highly complex nucleic acid sample in a continuous, isothermal reaction.

DETAILED DESCRIPTION OF THE INVENTION

Figure 1:
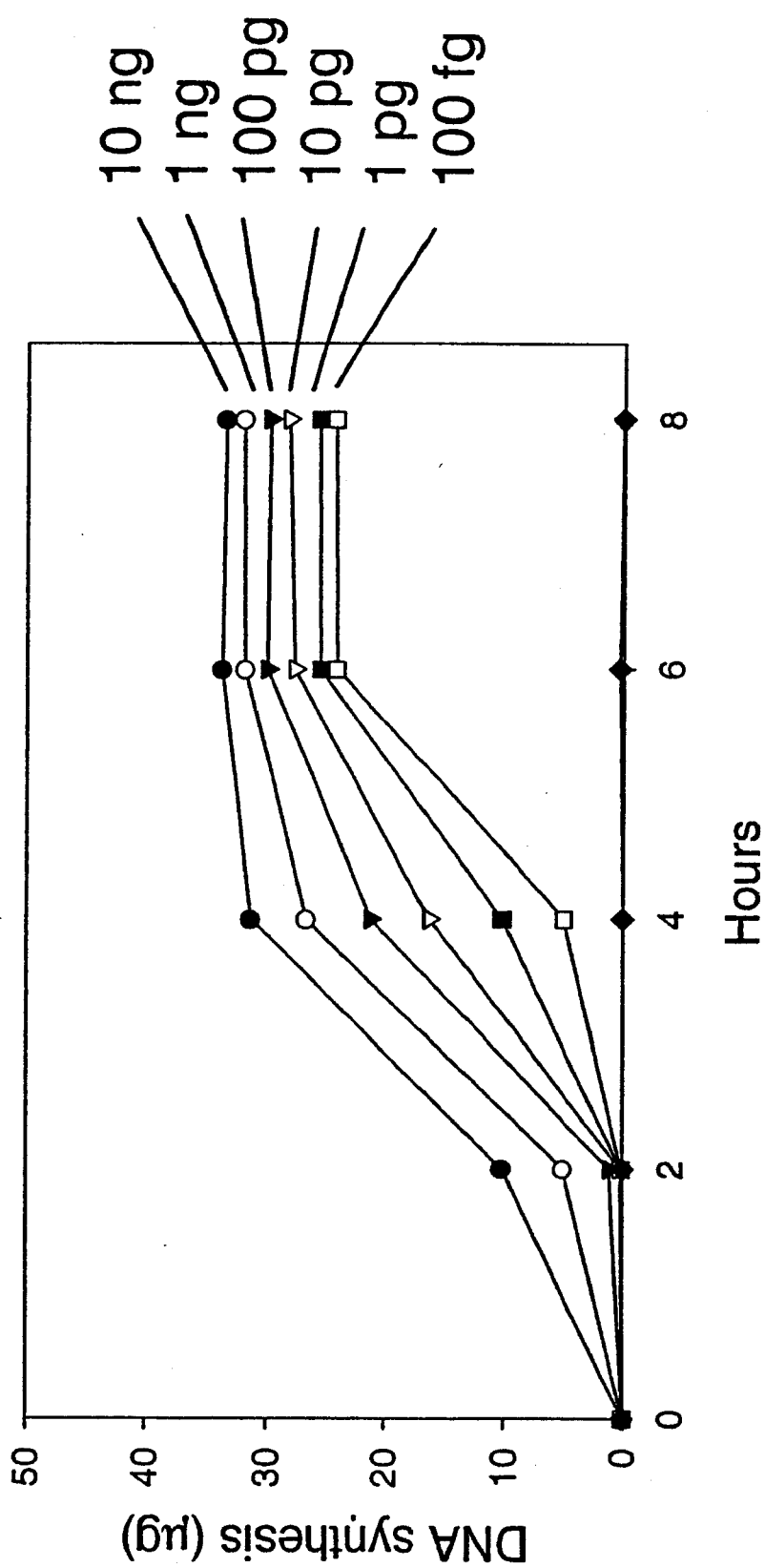
FIG. 1 is a graph of DNA synthesis (in μg) versus time (in hours) using different amounts of nucleic acid for amplification in the disclosed method.

The disclosed method makes use of certain materials and procedures which allow amplification of target nucleic acid sequences and whole genomes or other highly complex nucleic acid samples. These materials and procedures are described in detail below.

Materials

A. Target Sequence

The target sequence, which is the object of amplification, can be any nucleic acid. The target sequence can include multiple nucleic acid molecules, such as in the case of whole genome amplification, multiple sites in a nucleic acid molecule, or a single region of a nucleic acid molecule. For multiple strand displacement amplification, generally the target sequence is a single region in a nucleic acid molecule or nucleic acid sample. For whole genome amplification, the target sequence is the entire genome or nucleic acid sample. A target sequence can be in any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful target samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, acrude cell lysate samples, forensic samples, archeological samples, infection samples, nosocomial infection samples, production samples, drug preparation samples, biological molecule production samples, protein preparation samples, lipid preparation samples, ans/or carbohydrate preparation samples.

For multiple strand displacement amplification, preferred target sequences are those which are difficult to amplify using PCR due to, for example, length or composition. For whole genome amplification, preferred target sequences are nucleic acid samples from a single cell. For multiple strand displacement amplification of concatenated DNA the target is the concatenated DNA. The target sequence can be either one or both strands of cDNA. The target sequences for use in the disclosed method are preferably part of nucleic acid molecules or samples that are complex and non-repetitive (with the exception of the linkers in linker-concatenated DNA and sections of repetitive DNA in genomic DNA).

1. Target Sequences for Multiple Strand Displacement Amplification

Although multiple sites in a nucleic acid sample can be amplified simultaneously in the same MSDA reaction, for simplicity, the following discussion will refer to the features of a single nucleic acid sequence of interest which is to be amplified. This sequence is referred to below as a target sequence. It is preferred that a target sequence for MSDA include two types of target regions, an amplification target and a hybridization target. The hybridization target includes the sequences in the target sequence that are complementary to the primers in a set of primers. The amplification target is the portion of the target sequence which is to be amplified. For this purpose, the amplification target is preferably downstream of, or flanked by the hybridization target(s). There are no specific sequence or structural requirements for choosing a target sequence. The hybridization target and the amplification target within the target sequence are defined in terms of the relationship of the target sequence to the primers in a set of primers. The primers are designed to match the chosen target sequence. Although preferred, it is not required that sequences to be amplified and the sites of hybridization of the primers be separate since sequences in and around the sites where the primers hybridize will be amplified.

In multiple strand displacement amplification of circularized DNA, the circular DNA fragments are the amplification targets. The hybridization targets include the sequences that are complementary to the primers used for amplification. One form of circular DNA for amplification is circularized cDNA.

In multiple strand displacement amplification of linker-concatenated DNA, the DNA fragments joined by the linkers are the amplification targets and the linkers are the hybridization target. The hybridization targets (that is, the linkers) include the sequences that are complementary to the primers used for amplification. One form of concatenated DNA for amplification is concatenated cDNA.

B. Primers

Primers for use in the disclosed amplification method are oligonucleotides having sequence complementary to the target sequence. This sequence is referred to as the complementary portion of the primer. The complementary portion of a primer can be any length that supports specific and stable hybridization between the primer and the target sequence under the reaction conditions. Generally, for reactions at 37° C., this can be 10 to 35 nucleotides long or 16 to 24 nucleotides long. For whole genome amplification, the primers can be from 5 to 60 nucleotides long, and in particular, can be 5, 6, 7, 8, 9, 10, 11, 12, 13, 14, 15, 16, 17, 18, 19, and/or 20 nucleotides long.

For some forms of the disclosed method, such as those using primers or random or degenerate sequence (that is, use of a collection of primers having a variety of sequences), primer hybridization need not be specific. In such cases the primers need only be effective in priming synthesis. For example, in whole genome amplification specificity of priming is not essential since the goal generally is to amplify all sequences equally. Sets of random or degenerate primers can be composed of primers 5, 6, 7, 8, 9, 10, 11, 12, 13, 14, 15, 16, 17, 18, 19, and/or 20 nucleotides long or more. Primers six nucleotides long are referred to as hexamer primers. Preferred primers for whole genome amplification are random hexamer primers, for example, random hexamer primers where every possible six nucleotide sequence is represented in the set of primers. Similarly, sets of random primers of other particular lengths, or of a mixture of lengths preferably contain every possible sequence the length of the primer, or, in particular, the length of the complementary portion of the primer. Use of random primers is described in U.S. Pat. Nos. 5,043,272 and 6,214,587.

The disclosed primers can have one or more modified nucleotides. Such primers are referred to herein as modified primers. Modified primers have several advantages. First, some forms of modified primers, such as RNA/2'-O-methyl RNA chimeric primers, have a higher melting temperature (Tm) than DNA primers. This increases the stability of primer hybridization and will increase strand invasion by the primers. This will lead to more efficient priming. Also, since the primers are made of RNA, they will be exonuclease resistant. Such primers, if tagged with minor groove binders at their 5' end, will also have better strand invasion of the template dsDNA. In addition, RNA primers can also be very useful for WGA from biological samples such as cells or tissue. Since the biological samples contain endogenous RNA, this RNA can be degraded with RNase to generate a pool of random oligomers, which can then be used to prime the polymerase for amplification of the DNA. This eliminates any need to add primers to the reaction. Alternatively, DNase digestion of biological samples can generate a pool of DNA oligo primers for RNA dependent DNA amplification.

Chimeric primers can also be used. Chimeric primers are primers having at least two types of nucleotides, such as both deoxyribonucleotides and ribonucleotides, ribonucleotides and modified nucleotides, or two different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. The DNA and RNA portions of such primers can have random or degenerate sequences. Other forms of chimeric primers are, for example, 5'-(2'-O-Methyl)RNA-RNA-3' or 5'-(2'-O-Methyl)RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289–302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Primers composed, either in whole or in part, of nucleotides with universal bases are useful for reducing or eliminating amplification bias against repeated sequences in a target sample. This would be useful, for example, where a loss of sequence complexity in the amplified products is undesirable. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to $-O[(CH_2)nO]m\ CH_3$, $-O(CH_2)nOCH_3$, $-O(CH_2)nNH_2$, $-O(CH_2)nCH_3$, $-O(CH_2)n-ONH_2$, and $-O(CH_2)nON[(CH_2)nCH_3)]_2$, where n and m are from 1 to about 10.

Other modifications at the 2' position include but are not limted to: C1 to C10 lower alkyl, substituted lower alkyl, alkaryl, aralkyl, O-alkaryl or O-aralkyl, SH, $SCH_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497–1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can (and normally will) comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Primers may, but need not, also contain additional sequence at the 5' end of the primer that is not complementary to the target sequence. This sequence is referred to as the non-complementary portion of the primer. The non-complementary portion of the primer, if present, serves to facilitate strand displacement during DNA replication. The non-complementary portion of the primer can also include a functional sequence such as a promoter for an RNA polymerase. The non-complementary portion of a primer may be any length, but is generally 1 to 100 nucleotides long, and preferably 4 to 8 nucleotides long. The use of a non-complementary portion is not preferred when random or partially random primers are used for whole genome amplification.

1. Primers for Whole Genome Strand Displacement Amplification

In the case of whole genome strand displacement amplification, it is preferred that a set of primers having random or partially random nucleotide sequences be used. In a nucleic acid sample of significant complexity, which is the preferred target sequence for WGSDA, specific nucleic acid sequences present in the sample need not be known and the primers need not be designed to be complementary to any particular sequence. Rather, the complexity of the nucleic acid sample results in a large number of different hybridization target sequences in the sample which will be complementary to various primers of random or partially random sequence. The complementary portion of primers for use in WGSDA can be fully randomized, have only a portion that is randomized, or be otherwise selectively randomized.

The number of random base positions in the complementary portion of primers are preferably from 20% to 100% of the total number of nucleotides in the complementary portion of the primers. More preferably the number of random base positions are from 30% to 100% of the total number of nucleotides in the complementary portion of the primers. Most preferably the number of random base positions are from 50% to 100% of the total number of nucleotides in the complementary portion of the primers. Sets of primers having random or partially random sequences can be synthesized using standard techniques by allowing the addition of any nucleotide at each position to be randomized. It is also preferred that the sets of primers are composed of primers of similar length and/or hybridization characteristics.

2. Primers for Multiple Strand Displacement Amplification

In the case of multiple strand displacement amplification, the complementary portion of each primer is designed to be complementary to the hybridization target in the target sequence. In a set of primers, it is preferred that the complementary portion of each primer be complementary to a different portion of the target sequence. It is more preferred that the primers in the set be complementary to adjacent sites in the target sequence. It is also preferred that such adjacent sites in the target sequence are also adjacent to the amplification target in the target sequence.

It is preferred that, when hybridized to a target sequence, the primers in a set of primers are separated from each other. It is preferred that, when hybridized, the primers in a set of primers are separated from each other by at least 5 bases. It is more preferred that, when hybridized, the primers in a set of primers are separated from each other by at least 10 bases. It is still more preferred that, when hybridized, the primers in a set of primers are separated from each other by at least 20 bases. It is still more preferred that, when hybridized, the primers in a set of primers are separated from each other by at least 30 bases. It is still more preferred that, when hybridized, the primers in a set of primers are separated from each other by at least 40 bases. It is still more preferred that, when hybridized, the primers in a set of primers are separated from each other by at least 50 bases.

It is preferred that, when hybridized, the primers in a set of primers are separated from each other by no more than about 500 bases. It is more preferred that, when hybridized, the primers in a set of primers are separated from each other by no more than about 400 bases. It is still more preferred that, when hybridized, the primers in a set of primers are separated from each other by no more than about 300 bases. It is still more preferred that, when hybridized, the primers in a set of primers are separated from each other by no more than about 200 bases. Any combination of the preferred upper and lower limits of separation described above are specifically contemplated, including all intermediate ranges. The primers in a set of primers need not, when hybridized, be separated from each other by the same number of bases. It is preferred that, when hybridized, the primers in a set of primers are separated from each other by about the same number of bases.

The optimal separation distance between primers will not be the same for all DNA polymerases, because this parameter is dependent on the net polymerization rate. A processive DNA polymerase will have a characteristic polymerization rate which may range from 5 to 300 nucleotides per second, and may be influenced by the presence or absence of accessory ssDNA binding proteins and helicases. In the case of a non-processive polymerase, the net polymerization rate will depend on the enzyme concentration, because at higher concentrations there are more re-initiation events and thus the net polymerization rate will be increased. An example of a processive polymerase is $\phi$29 DNA polymerase, which proceeds at 50 nucleotides per second. An example of a non-processive polymerase is Vent exo(−) DNA polymerase, which will give effective polymerization rates of 4 nucleotides per second at low concentration, or 16 nucleotides per second at higher concentrations.

To obtain an optimal yield in an MSDA reaction, the primer spacing is preferably adjusted to suit the polymerase being used. Long primer spacing is preferred when using a polymerase with a rapid polymerization rate. Shorter primer spacing is preferred when using a polymerase with a slower polymerization rate. The following assay can be used to determine optimal spacing with any polymerase. The assay uses sets of primers, with each set made up of 5 left primers and 5 right primers. The sets of primers are designed to hybridize adjacent to the same target sequence with each of the different sets of primers having a different primer spacing. The spacing is varied systematically between the sets of primers in increments of 25 nucleotides within the range of 25 nucleotides to 400 nucleotides (the spacing of the primers within each set is the same). A series of reactions are performed in which the same target sequence is amplified using the different sets of primers. The spacing that produces the highest experimental yield of DNA is the optimal primer spacing for the specific DNA polymerase, or DNA polymerase plus accessory protein combination being used.

DNA replication initiated at the sites in the target sequence where the primers hybridize will extend to and displace strands being replicated from primers hybridized at adjacent sites. Displacement of an adjacent strand makes it available for hybridization to another primer and subsequent initiation of another round of replication. The region(s) of the target sequence to which the primers hybridize is referred to as the hybridization target of the target sequence.

A set of primers can include any desired number of primers of different nucleotide sequence. For MSDA, it is preferred that a set of primers include a plurality of primers. It is more preferred that a set of primers include 3 or more primers. It is still more preferred that a set of primers include 4 or more, 5 or more, 6 or more, or 7 or more primers. In general, the more primers used, the greater the level of amplification that will be obtained. There is no fundamental upper limit to the number of primers that a set of primers can have. However, for a given target sequence, the number of primers in a set of primers will generally be limited to the number of hybridization sites available in the target sequence. For example, if the target sequence is a 10,000 nucleotide DNA molecule and 20 nucleotide primers are used, there are 500 non-overlapping 20 nucleotide sites in the target sequence. Even more primers than this could be used if overlapping sites are either desired or acceptable. It is preferred that a set of primers include no more than about 300 primers. It is preferred that a set of primers include no more than about 200 primers. It is still more preferred that a set of primers include no more than about 100 primers. It is more preferred that a set of primers include no more than about 50 primers. It is most preferred that a set of primers include from 7 to about 50 primers. Any combination of the preferred upper and lower limits for the number of primers in a set of primers described above are specifically contemplated, including all intermediate ranges.

A preferred form of primer set for use in MSDA includes two sets of primers, referred to as a right set of primers and a left set of primers. The right set of primers and left set of primers are designed to be complementary to opposite strands of a target sequence. It is preferred that the complementary portions of the right set of primers are each complementary to the right hybridization target, and that each is complementary to a different portion of the right hybridization target. It is preferred that the complementary portions of the left set of primers are each complementary to the left hybridization target, and that each is complementary to a different portion of the left hybridization target. The right and left hybridization targets flank opposite ends of the amplification target in a target sequence. It is preferred that a right set of primers and a left set of primers each include a preferred number of primers as described above for a set of primers. Specifically, it is preferred that a right or left set of primers include a plurality of primers. It is more preferred that a right or left set of primers include 3 or more primers. It is still more preferred that a right or left set of primers include 4 or more, 5 or more, 6 or more, or 7 or more primers. It is preferred that a right or left set of primers include no more than about 200 primers. It is more preferred that a right or left set of primers include no more than about 100 primers. It is most preferred that a right or left set of primers include from 7 to about 100 primers. Any combination of the preferred upper and lower limits for the number of primers in a set of primers described above are specifically contemplated, including all intermediate ranges. It is also preferred that, for a given target sequence, the right set of primers and the left set of primers include the same number of primers. It is also preferred that, for a given target sequence, the right set of primers and the left set of primers are composed of primers of similar length and/or hybridization characteristics.

Where the target sequence(s) are present in mixed sample—for example, a nosocomial sample containing both human and non-human nucleic acids—the primers used can be specific for the nucleic acids of interest. Thus, to detect pathogen (that is, non-human) nucleic acids in a patient sample, primers specific to pathogen nucleic acids can be used. If human nucleic acids are to be detected, then primers specific to human nucleic acids can be used. In this context, primers specific for particular target nucleic acids or target sequences or a particular class of target nucleic acids or target sequences refer to primers that support amplification of the target nucleic acids and target sequences but do not support substantial amplification of non-target nucleic acids or sequences that are in the relevant sample 3. Detection Tags The non-complementary portion of a primer can include sequences to be used to further manipulate or analyze amplified sequences. An example of such a sequence is a detection tag, which is a specific nucleotide sequence present in the non-complementary portion of a primer. Detection tags have sequences complementary to detection probes. Detection tags can be detected using their cognate detection probes. Detection tags become incorporated at the ends of amplified strands. The result is amplified DNA having detection tag sequences that are complementary to the complementary portion of detection probes. If present, there may be one, two, three, or more than three detection tags on a primer. It is preferred that a primer have one, two, three or four detection tags. Most preferably, a primer will have one detection tag. Generally, it is preferred that a primer have 10 detection tags or less. There is no fundamental limit to the number of detection tags that can be present on a primer except the size of the primer. When there are multiple detection tags, they may have the same sequence or they may have different sequences, with each different sequence complementary to a different detection probe. It is preferred that a primer contain detection tags that have the same sequence such that they are all complementary to a single detection probe. For some multiplex detection methods, it is preferable that primers contain up to six detection tags and that the detection tag portions have different sequences such that each of the detection tag portions is complementary to a different detection probe. A similar effect can be achieved by using a set of primers where each has a single different detection tag. The detection tags can each be any length that supports specific and stable hybridization between the detection tags and the detection probe. For this purpose, a length of 10 to 35 nucleotides is preferred, with a detection tag portion 15 to 20 nucleotides long being most preferred.

4. Address Tag

Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. It is preferred that a primer have one or two address tags. Most preferably, a primer will have one address tag. Generally, it is preferred that a primer have 10 address tags or less. There is no fundamental limit to the number of address tags that can be present on a primer except the size of the primer. When there are multiple address tags, they may have the same sequence or they may have different sequences, with each different sequence complementary to a different address probe. It is preferred that a primer contain address tags that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

C. Nucleic Acid Fingerprints

The disclosed method can be used to produce replicated strands that serve as a nucleic acid fingerprint of a complex sample of nucleic acid. Such a nucleic acid fingerprint can be compared with other, similarly prepared nucleic acid fingerprints of other nucleic acid samples to allow convenient detection of differences between the samples. The nucleic acid fingerprints can be used both for detection of related nucleic acid samples and comparison of nucleic acid samples. For example, the presence or identity of specific organisms can be detected by producing a nucleic acid fingerprint of the test organism and comparing the resulting nucleic acid fingerprint with reference nucleic acid fingerprints prepared from known organisms. Changes and differences in gene expression patterns can also be detected by preparing nucleic acid fingerprints of mRNA from different cell samples and comparing the nucleic acid fingerprints.

The replicated strands can also be used to produce a set of probes or primers that is specific for the source of a nucleic acid sample. The replicated strands can also be used as a library of nucleic acid sequences present in a sample. Nucleic acid fingerprints can be made up of, or derived from, whole genome amplification of a sample such that the entire relevant nucleic acid content of the sample is substantially represented, or from multiple strand displacement amplification of selected target sequences within a sample.

Nucleic acid fingerprints can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of nucleic acid fingerprints include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from nucleic acid fingerprints and replicated strands produced in the disclosed method can also be collected, used, saved, stored, and/or archived.

Nucleic acid fingerprints can also contain or be made up of other information derived from the information generated in the disclosed method, and can be combined with information obtained or generated from any other source. The informational nature of nucleic acid fingerprints produced using the disclosed method lends itself to combination and/or analysis using known bioinformatics systems and methods.

Nucleic acid fingerprints of nucleic acid samples can be compared to a similar nucleic acid fingerprint derived from any other sample to detect similarities and differences in the samples (which is indicative of similarities and differences in the nucleic acids in the samples). For example, a nucleic acid fingerprint of a first nucleic acid sample can be compared to a nucleic acid fingerprint of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and Salmonella. A different type of tissue refers to tissues of different types such as liver and kidney, or skin and brain. A different strain or species of organism refers to organisms differing in their species or strain designation as those terms are understood in the art.

D. Solid-State Detectors

Solid-state detectors are solid-state substrates or supports to which address probes or detection molecules have been coupled. A preferred form of solid-state detector is an array detector. An array detector is a solid-state detector to which multiple different address probes or detection molecules have been coupled in an array, grid, or other organized pattern.

Solid-state substrates for use in solid-state detectors can include any solid material to which oligonucleotides can be coupled. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin films or membranes, beads, bottles, dishes, fibers, optical fibers, woven fibers, chips, compact disks, shaped polymers, particles and microparticles. A chip is a rectangular or square small piece of material. Preferred forms for solid-state substrates are thin films, beads, or chips.

Address probes immobilized on a solid-state substrate allow capture of the products of the disclosed amplification method on a solid-state detector. Such capture provides a convenient means of washing away reaction components that might interfere with subsequent detection steps. By attaching different address probes to different regions of a solid-state detector, different amplification products can be captured at different, and therefore diagnostic, locations on the solid-state detector. For example, in a multiplex assay, address probes specific for numerous different amplified nucleic acids (each representing a different target sequence amplified via a different set of primers) can be immobilized in an array, each in a different location. Capture and detection will occur only at those array locations corresponding to amplified nucleic acids for which the corresponding target sequences were present in a sample.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994), and Khrapko et al., *Mol Biol* (Mosk) (USSR) 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Examples of nucleic acid chips and arrays, including methods of making and using such chips and arrays, are described in U.S. Pat. Nos. 6,287,768, 6,288,220, 6,287,776, 6,297,006, and 6,291,193.

E. Solid-State Samples

Solid-state samples are solid-state substrates or supports to which target sequences or MDA products (that is, replicated strands) have been coupled or adhered. Target sequences are preferably delivered in a target sample or assay sample. A preferred form of solid-state sample is an array sample. An array sample is a solid-state sample to which multiple different target sequences have been coupled or adhered in an array, grid, or other organized pattern.

Solid-state substrates for use in solid-state samples can include any solid material to which target sequences can be coupled or adhered. This includes materials such as acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin films or membranes, beads, bottles, dishes, slides, fibers, optical fibers, woven fibers, chips, compact disks, shaped polymers, particles and microparticles. A chip is a rectangular or square small piece of material. Preferred forms for solid-state substrates are thin films, beads, or chips.

Target sequences immobilized on a solid-state substrate allow formation of target-specific amplified nucleic acid localized on the solid-state substrate. Such localization provides a convenient means of washing away reaction components that might interfere with subsequent detection steps, and a convenient way of assaying multiple different samples simultaneously. Amplified nucleic acid can be independently formed at each site where a different sample is adhered. For immobilization of target sequences or other oligonucleotide molecules to form a solid-state sample, the methods described above can be used. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

A preferred form of solid-state substrate is a glass slide to which up to 256 separate target samples have been adhered as an array of small dots. Each dot is preferably from 0.1 to 2.5 mm in diameter, and most preferably around 2.5 mm in diameter. Such microarrays can be fabricated, for example, using the method described by Schena et al., *Science* 270:487–470 (1995). Briefly, microarrays can be fabricated on poly-L-lysine-coated microscope slides (Sigma) with an arraying machine fitted with one printing tip. The tip is loaded with 1 µl of a DNA sample (0.5 mg/ml) from, for example, 96-well microtiter plates and deposited ~0.005 µl per slide on multiple slides at the desired spacing. The printed slides can then be rehydrated for 2 hours in a humid chamber, snap-dried at 100° C. for 1 minute, rinsed in 0.1% SDS, and treated with 0.05% succinic anhydride prepared in buffer consisting of 50% 1-methyl-2-pyrrolidinone and 50% boric acid. The DNA on the slides can then be denatured in, for example, distilled water for 2 minutes at 90° C. immediately before use. Microarray solid-state samples can scanned with, for example, a laser fluorescent scanner with a computer-controlled XY stage and a microscope objective. A mixed gas, multiline laser allows sequential excitation of multiple fluorophores.

F. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodarmine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodanine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217–230 (1993)), aminoallyldeoxyuridine (Henegariu et al., *Nature Biotechnology* 18:345–348 (2000)), 5-methylcytosine (Sano et al., *Biochim. Biophys. Acta* 951:157–165 (1988)), bromouridine (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.,* 22:3226–3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo[$3.3.1.1^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

G. Detection Probes

Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnol.* 14:303–309 (1995)). The use of such probes eliminates the need for removal of unhybridized probes prior to label detection because the unhybridized detection probes will not produce a signal. This is especially useful in multiplex assays.

H. Address Probes

An address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

I. Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et a. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253–1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291–3296) or the phosphotriester method as described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994). Other forms of oligonucleotide synthesis are described in U.S. Pat. Nos. 6,294,664 and 6,291,669.

The nucleotide sequence of an oligonucleotide is generally determined by the sequential order in which subunits of subunit blocks are added to the oligonucleotide chain during synthesis. Each round of addition can involve a different, specific nucleotide precursor or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oilgonucleotide if that position is to be degenerate for A and T. Precursors for all four nucleotides can be included for a fully degenerate or random position. Completely random oligonucleotides an be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

Hexamer oligonucleotides were synthesized on a Persepative Biosystems 8909 Expedite Nucleic Acid Synthesis system using standard β-cyanoethyl phosphoramidite coupling chemistry on mixed dA+dC+dG+dT synthesis columns (Glen Research, Sterling, Va.). The four phosphoramidites were mixed in equal proportions to randomize the bases at each position in the oligonucleotide. Oxidation of the newly formed phosphites were carried out using the sulfurizing reagent 3H-1,2-benzothiole-3-one-1,1-idoxide (Glen Research) instead of the standard oxidizing reagent after the first and second phosphoramidite addition steps. The thio-phosphitylated oligonucleotides were deprotected using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

J. DNA Polymerases

DNA polymerases useful in multiple displacement amplification must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are bacteriophage φ29 DNA polymerase (U.S. Pat. Nos. 5,198,543 and 5,001,050 to Blanco et al.), Bst large fragment DNA polymerase (Exo(−) Bst; Aliotta et al., *Genet. Anal.* (Netherlands) 12:185–195 (1996)) and exo(−)Bca DNA polymerase (Walker and Linn, *Clinical Chemistry* 42:1604–1608 (1996)). Other useful polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), Sequenase (U.S. Biochemicals), PRD1 DNA polymerase (Zhu and Ito, *Biochim. Biophys. Acta.* 1219:267–276 (1994)), and T4 DNA polymerase holoenzyme (Kaboord and Benkovic, *Curr. Biol.* 5:149–157 (1995)). φ29 DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2): 711–715 (1993); Skaliter and Lehman, *Proc. Natl. Acad. Sci. USA* 91(22):10665–10669 (1994)); single-stranded DNA binding proteins (SSB; Rigler and Romano, *J. Biol. Chem.* 270:8910–8919 (1995)); phage T4 gene 32 protein (Villemain and Giedroc, *Biochemistry* 35:14395–14404 (1996); and calf thymus helicase (Siegel et al., *J. Biol. Chem.* 267:13629–13635 (1992)).

The ability of a polymerase to carry out strand displacement replication can be determined by using the polymerase in a strand displacement replication assay such as those described in Examples 1 and 5. The assay in the examples can be modified as appropriate. For example, a helicase can be used instead of SSB. Such assays should be performed at a temperature suitable for optimal activity for the enzyme being used, for example, 32° C. for φ29 DNA polymerase, from 46° C. to 64° C. for exo(−) Bst DNA polymerase, or from about 60° C. to 70° C. for an enzyme from a hyperthermophylic organism. For assays from 60° C. to 70° C., primer length may be increased to provide a melting temperature appropriate for the assay temperature. Another useful assay for selecting a polymerase is the primer-block assay described in Kong et al., *J. Biol. Chem.* 268:1965–1975 (1993). The assay consists of a primer extension assay using an M13 ssDNA template in the presence or absence of an oligonucleotide that is hybridized upstream of the extending primer to block its progress. Enzymes able to displace the blocking primer in this assay are expected to be useful for the disclosed method.

The materials described above can be packaged together in any suitable combination as a kit useful for performing the disclosed method.

Method

The disclosed method is based on strand displacement replication of the nucleic acid sequences by multiple primers. The method can be used to amplify one or more specific sequences (multiple strand displacement amplification), an entire genome or other DNA of high complexity (whole genome strand displacement amplification), or concatenated DNA (multiple strand displacement amplification of concatenated DNA). The disclosed method generally involves hybridization of primers to a target nucleic acid sequence and replication of the target sequence primed by the hybridized primers such that replication of the target sequence results in replicated strands complementary to the target sequence. During replication; the growing replicated strands displace other replicated strands from the target sequence (or from another replicated strand) via strand displacement replication. As used herein, a replicated strand is a nucleic acid strand resulting from elongation of a primer hybridized to a target sequence or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of a target sequence to be made in a single, isothermic reaction.

Denaturation of nucleic acid molecules to be amplified is common in amplification techniques. This is especially true when amplifying genomic DNA. In particular, PCR uses multiple denaturation cycles. Denaturation is generally used to make nucleic acid strands accessible to primers. It was discovered that the target nucleic acids, genomic DNA, for example, need not be denatured [*] for efficient multiple displacement amplification. It was also discovered that elimination of a denaturation step and denaturation conditions has additional advantages such as reducing sequence bias in the amplified products. In preferred forms of the disclosed method, the nucleic acid sample or template nucleic acid is not subjected to denaturating conditions and/or no denaturation step is used. In some forms of the disclosed method, the nucleic acid sample or template nucleic acid is not subjected to heat denaturating conditions and/or no heat denaturation step is used. It should be understood that while sample preparation (for example, cell lysis and processing of cell extracts) may involve conditions that might be considered denaturing (for example, treatment with alkali), the denaturation conditions or step eliminated in some forms of the disclosed method refers to denaturation steps or conditions intended and used to make nucleic acid strands accessible to primers. Such denaturation is commonly a heat denaturation, but can also be other forms of denaturation such as chemical denaturation. It should be understood that in the disclosed method where the nucleic acid sample or template nucleic acid is not subjected to denaturing conditions, the template strands are accessible to the primers (since amplification occurs). However, the template stands are not made accessible via general denaturation of the sample or template nucleic acids.

The efficiency of a DNA amplification procedure may be described for individual loci as the percent representation, where the percent representation is 100% for a locus in genomic DNA as purified from cells. For 10,000-fold amplification, the average representation frequency was 141% for 8 loci in DNA amplified without heat denaturation of the template, and 37% for the 8 loci in DNA amplified with heat denaturation of the template. The omission of a heat denaturation step results in a 3.8-fold increase in the representation frequency for amplified loci. Amplification bias may be calculated between two samples of amplified DNA or between a sample of amplified DNA and the template DNA it was amplified from. The bias is the ratio between the values for percent representation for a particular locus. The maximum bias is the ratio of the most highly represented locus to the least represented locus. For 10,000-fold amplification, the maximum amplification bias was 2.8 for DNA amplified without heat denaturation of the template, and 50.7 for DNA amplified with heat denaturation of the template. The omission of a heat denaturation step results in an 18-fold decrease in the maximum bias for amplified loci.

In another form of the method, the primers can be hexamer primers. It was discovered that such short, 6 nucleotide primers can still prime multiple strand displacement replication efficiently. Such short primers are easier to produce as a complete set of primers of random sequence (random primers) than longer primers at least because there are fewer to make. In another form of the method, the primers can each contain at least one modified nucleotide such that the primers are nuclease resistant. In another form of the method, the primers can each contain at least one modified nucleotide such that the melting temperature of the primer is altered relative to a primer of the same sequence without the modified nucleotide(s). In another form of the method, the DNA polymerase can be φ29 DNA polymerase. It was discovered that φ29 DNA polymerase produces greater amplification in multiple displacement amplification. The combination of two or more of the above features also yields improved results in multiple displacement amplification. In a preferred embodiment, for example, the target sample is not subjected to denaturing conditions, the primers are hexamer primers and contain modified nucleotides such that the primers are nuclease resistant, and the DNA polymerase is φ29 DNA polymerase. The above features are especially useful in whole genome strand displacement amplification (WGSDA).

In another form of the disclosed method, the method includes labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

Some forms of the disclosed method provide amplified DNA of higher quality relative to previous methods due to the lack of a heat denaturation treatment of the DNA that is the target for amplification. Thus, the template DNA does not undergo the strand breakage events caused by heat treatment and the amplification that is accomplished by a single DNA polymerase extends farther along template strands of increased length.

In one form of the disclosed method, a small amount of purified double-strand human genomic DNA (1 ng, for example) can be mixed with exonuclease-resistant random hexamer primers and φ29 DNA polymerase under conditions that favor DNA synthesis. For example, the mixture can simply be incubated at 30° C. and multiple displacement amplification will take place. Thus, any single-stranded or duplex DNA may be used, without any additional treatment, making the disclosed method a simple, one-step procedure. Since so little DNA template is required, a major advantage of the disclosed method is that DNA template may be taken from preparations that contain levels of contaminants that would inhibit other DNA amplification procedures such as PCR. For MDA the sample may be diluted so that the contaminants fall below the concentration at which they would interfere with the reaction. The disclosed method can be performed (and the above advantages acheived) using any type of sample, including, for example, bodily fluids such as urine, semen, lymphatic fluid, cerebrospinal fluid, and amniotic fluid.

The need for only small amounts of DNA template in the disclosed method means that the method is useful for DNA amplification from very small samples. In particular, the disclosed method may be used to amplify DNA from a single cell. The ability to obtain analyzable amounts of nucleic acid from a single cell (or similarly small sample) has many applications in preparative, analytical, and diagnostic procedures such as prenatal diagnostics. Other examples of biological samples containing only small amounts of DNA for which amplification by the disclosed method would be useful are material excised from tumors or other archived medical samples, needle aspiration biopsies, clinical samples arising from infections, such as nosocomial infections, forensic samples, or museum specimens of extinct species.

More broadly, the disclosed method is useful for applications in which the amounts of DNA needed are greater than the supply. For example, procedures that analyze DNA by chip hybridization techniques are limited by the amounts of DNA that can be purified from typically sized blood samples. As a result many chip hybridization procedures utilize PCR to generate a sufficient supply of material for the high-throughput procedures. The disclosed method presents a useful technique for the generation of plentiful amounts of amplified DNA that faithfully reproduces the locus representation frequencies of the starting material.

A specific embodiment of the disclosed method is described in Example 1, wherein whole genome amplification is performed by MDA without heat treatment of the human template DNA. As shown in the example, the disclosed method produces a DNA amplification product with improved performance in genetic assays compared to amplification performed with heat treatment of the template DNA. The longer DNA products produced without heat treatment of the template yield larger DNA fragments in Southern blotting and genetic analysis using RFLP.

The breakage of DNA strands by heat treatment is demonstrated directly in Example 2, while the decreased rate and yield of DNA amplification from heat-treated DNA is depicted in Example 3. The decrease in DNA product strand length resulting from heat treatment of the DNA template is demonstrated in Example 4.

A specific form of the disclosed method is described in Example 5, wherein purified human genomic DNA is amplified by MDA without heat treatment of the template. As shown in the example, the disclosed method produces for a DNA amplification product with no loss of locus representation when used as a substrate in quantitative PCR assays compared to DNA amplified with heat treatment of the template.

Another specific form of the disclosed method is described in Example 6, wherein purified human genomic DNA is amplified by MDA without heat treatment of the template. As shown in the example, the disclosed method produces a DNA amplification product with a low amplification bias, with the variation in representation among eight different loci varying by less than 3.0. In contrast, the amplification bias of DNA products amplified by two PCR-based amplification methods, PEP and DOP-PCR, varies between two and six orders of magnitude.

Another specific form of the disclosed method is described in Example 7, wherein the amplification of c-jun sequences using specific, nested primers from a human genomic DNA template is enhanced by omission of a DNA template heat denaturation step.

Another specific form of the disclosed method is described in Example 8, wherein human genomic DNA is amplified in the absence of a heat treatment step directly from whole blood or from tissue culture cells with the same efficiency as from purified DNA. The DNA amplified directly from blood or cells has substantially the same locus representation values as DNA amplified from purified human DNA template. This represents an advantage over other amplification procedures such as PCR, since components such as heme in whole blood inhibit PCR and necessitate a purification step before DNA from blood can be used as a PCR template.

Another specific form of the disclosed method is described in Example 9, wherein purified human genomic DNA is amplified by MDA without heat treatment of the template in the presence of 70% AA-dUTP/30% dTTP. As shown in the example, the disclosed method provides for a DNA amplification product with the same low amplification bias as for DNA amplified in the presence of 100% dTTP.

A. Whole Genome Strand Displacement Amplification

In one form of the method, referred to as whole genome strand displacement amplification (WGSDA), a random or partially random set of primers is used to randomly prime a sample of genomic nucleic acid (or another sample of nucleic acid of high complexity). By choosing a sufficiently large set of primers of random or mostly random sequence, the primers in the set will be collectively, and randomly, complementary to nucleic acid sequences distributed throughout nucleic acid in the sample. Amplification proceeds by replication with a processive polymerase initiated at each primer and continuing until spontaneous termination. A key feature of this method is the displacement of intervening primers during replication by the polymerase. In this way, multiple overlapping copies of the entire genome can be synthesized in a short time.

Whole genome strand displacement amplification can be performed by (a) mixing a set of random or partially random primers with a genomic sample (or other nucleic acid sample of high complexity), to produce a primer-target sample mixture, and incubating the primer-target sample mixture under conditions that promote hybridization between the primers and the genomic DNA in the primer-target sample mixture, and (b) mixing DNA polymerase with the primer-target sample mixture, to produce a polymerase-target sample mixture, and incubating the polymerase-target sample mixture under conditions that promote replication of the genomic DNA. Strand displacement replication is preferably accomplished by using a strand displacing DNA polymerase or a DNA polymerase in combination with a compatible strand displacement factor.

The method has advantages over the polymerase chain reaction since it can be carried out under isothermal conditions. Other advantages of whole genome strand displacement include a higher level of amplification than whole genome PCR, amplification is less sequence-dependent than PCR, a lack of re-annealing artifacts or gene shuffling artifacts as can occur with PCR (since there are no cycles of denaturation and re-annealing), and a lower amplification bias than PCR-based genome amplification (bias of 3-fold for WGSDA versus 20- to 60-fold for PCR-based genome amplification).

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction.

It is preferred that the set of primers used for WGSDA be used at concentrations that allow the primers to hybridize at desired intervals within the nucleic acid sample. For example, by using a set of primers at a concentration that allows them to hybridize, on average, every 4000 to 8000 bases, DNA replication initiated at these sites will extend to and displace strands being replicated from adjacent sites. It should be noted that the primers are not expected to hybridize to the target sequence at regular intervals. Rather, the average interval will be a general function of primer concentration. Primers for WGSDA can also be formed from RNA present in the sample. By degrading endogenous RNA with RNase to generate a pool of random oligomers, the random oligomers can then be used by the polymerase for amplification of the DNA. This eliminates any need to add primers to the reaction. Alternatively, DNase digestion of biological samples can generate a pool of DNA oligo primers for RNA dependent DNA amplification.

As in multiple strand displacement amplification, displacement of an adjacent strand makes it available for hybridization to another primer and subsequent initiation of another round of replication. The interval at which primers in the set of primers hybridize to the target sequence determines the level of amplification. For example, if the average interval is short, adjacent strands will be displaced quickly and frequently. If the average interval is long, adjacent strands will be displaced only after long runs of replication.

In the disclosed method, the DNA polymerase catalyzes primer extension and strand displacement in a processive strand displacement polymerization reaction that proceeds as long as desired. Preferred strand displacing DNA polymerases are bacteriophage $\phi$29 DNA polymerase (U.S. Pat. Nos. 5,198,543 and 5,001,050 to Blanco et al.), large fragment Bst DNA polymerase (Exo(−) Bst), exo(−)Bca DNA polymerase, and Sequenase. During strand displacement replication one may additionally include radioactive, or modified nucleotides such as bromodeoxyuridine triphosphate, in order to label the DNA generated in the reaction. Alternatively, one may include suitable precursors that provide a binding moiety such as biotinylated nucleotides (Langer et al., *Proc. Natl. Acad. Sci. USA* 78:6633 (1981)).

Genome amplification using PCR, and uses for the amplified DNA, is described in Zhang et al., *Proc. Natl. Acad. Sci. USA* 89:5847–5851 (1992), Telenius et al., *Genomics* 13:718–725 (1992), Cheung et al., *Proc. Natl. Acad. Sci. USA* 93:14676–14679 (1996), and Kukasjaarvi et al., *Genes, Chromosomes and Cancer* 18:94–101 (1997). The uses of the amplified DNA described in these publications are also generally applicable to DNA amplified using the disclosed methods. Whole Genome Strand Displacement Amplification, unlike PCR-based whole genome amplification, is suitable for haplotype analysis since WGSDA yields longer fragments than PCR-based whole genome amplification. PCR-based whole genome amplification is also less suitable for haplotype analysis since each cycle in PCR creates an opportunity for priming events that result in the association of distant sequences (in the genome) to be put together in the same fragment.

B. Multiple Strand Displacement Amplification

In one preferred form of the method, referred to as multiple strand displacement amplification (MSDA), two sets of primers are used, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The 5' end of primers in both sets are distal to the nucleic acid sequence of interest when the primers are hybridized to the flanking sequences in the nucleic acid molecule. Preferably, each member of each set has a portion complementary to a separate and non-overlapping nucleotide sequence flanking the target nucleotide sequence. Amplification proceeds by replication initiated at each primer and continuing through the target nucleic acid sequence. A key feature of this method is the displacement of intervening primers during replication. Once the nucleic acid strands elongated from the right set of primers reaches the region of the nucleic acid molecule to which the left set of primers hybridizes, and vice versa, another round of priming and replication will take place. This allows multiple copies of a nested set of the target nucleic acid sequence to be synthesized in a short period of time.

Multiple strand displacement amplification can be performed by (a) mixing a set of primers with a target sample, to produce a primer-target sample mixture, and incubating the primer-target sample mixture under conditions that promote hybridization between the primers and the target sequence in the primer-target sample mixture, and (b) mixing DNA polymerase with the primer-target sample mixture, to produce a polymerase-target sample mixture, and incubating the polymerase-target sample mixture under conditions that promote replication of the target sequence. Strand displacement replication is preferably accomplished by using a strand displacing DNA polymerase or a DNA polymerase in combination with a compatible strand displacement factor.

By using a sufficient number of primers in the right and left sets, only a few rounds of replication are required to produce hundreds of thousands of copies of the nucleic acid sequence of interest. For example, it can be estimated that, using right and left primer sets of 26 primers each, 200,000 copies of a 5000 nucleotide amplification target can be produced in 10 minutes (representing just four rounds of priming and replication). It can also be estimated that, using right and left primer sets of 26 primers each, 200,000 copies of a 47,000 nucleotide amplification target can be produced in 60 minutes (again representing four rounds of priming and replication). These calculations are based on a polymerase extension rate of 50 nucleotides per second. It is emphasized that reactions are continuous and isothermal— no cycling is required.

The disclosed method has advantages over the polymerase chain reaction since it can be carried out under isothermal conditions. No thermal cycling is needed because the polymerase at the head of an elongating strand (or a compatible strand-displacement factor) will displace, and thereby make available for hybridization, the strand ahead of it. Other advantages of multiple strand displacement amplification include the ability to amplify very long nucleic acid segments (on the order of 50 kilobases) and rapid amplification of shorter segments (10 kilobases or less). Long nucleic acid segments can be amplified in the disclosed method since there is no cycling which could interrupt continuous synthesis or allow the formation of artifacts due to rehybridization of replicated strands. In multiple strand displacement amplification, single priming events at unintended sites will not lead to artifactual amplification at these sites (since amplification at the intended site will quickly outstrip the single strand replication at the unintended site).

In another form of the method, referred to as gene specific strand displacement amplification (GS-MSDA), target DNA is first digested with a restriction endonuclease. The digested fragments are then ligated end-to-end to form DNA circles. These circles can be monomers or concatemers. Two sets of primers are used for amplification, a right set and a left set. Primers in the right set of primers each have a portion complementary to nucleotide sequences flanking one side of a target nucleotide sequence and primers in the left set of primers each have a portion complementary to nucleotide sequences flanking the other side of the target nucleotide sequence. The primers in the right set are complementary to one strand of the nucleic acid molecule containing the target nucleotide sequence and the primers in the left set are complementary to the opposite strand. The primers are designed to cover all or part of the sequence needed to be amplified. Preferably, each member of each set has a portion complementary to a separate and non-overlapping nucleotide sequence flanking the target nucleotide sequence. Amplification proceeds by replication initiated at each primer and continuing through the target nucleic acid sequence. In one form of GS-MSDA, referred to as linear GS-MSDA, amplification is performed with a set of primers complementary to only one strand, thus amplifying only one of the strands. In another form of GS-MSDA, cDNA sequences can be circularized to form single stranded DNA circles. Amplification is then performed with a set of primers complementary to the single-stranded circular cDNA.

C. Multiple Strand Displacement Amplification of Concatenated DNA

In another form of the method, referred to as multiple strand displacement amplification of concatenated DNA (MSDA-CD), concatenated DNA is amplified. A preferred form of concatenated DNA is concatenated cDNA. Concatenated DNA can be amplified using a random or partially random set of primers, as in WGSDA, or using specific primers complementary to specific hybridization targets in the concatenated DNA. MSDA-CD is preferred for amplification of a complex mixture or sample of relatively short nucleic acid samples (that is, fragments generally in the range of 100 to 6,000 nucleotides). Messenger RNA is the most important example of such a complex mixture. MSDA-CD provides a means for amplifying all cDNAs in a cell is equal fashion. Because the concatenated cDNA can be amplified up to 5,000-fold, MSDA-CD will permit RNA profiling analysis based on just a few cells. To perform MSDA-CD, DNA must first be subjected to a concatenation step. If an RNA sample (such as mRNA) is to be amplified, the RNA is first converted to a double-stranded cDNA using standard methods. The cDNA, or any other set of DNA fragments to be amplified, is then converted into a DNA concatenate, preferably with incorporation of linkers.

D. Modifications and Additional Operations

1. Detection of Amplification Products

Amplification products can be detected directly by, for example, primary labeling or secondary labeling, as described below.

i. Primary Labeling

Primary labeling consists of incorporating labeled moieties, such as fluorescent nucleotides, biotinylated nucleotides, digoxygenin-containing nucleotides, or bromodeoxyuridine, during strand displacement replication. For example, one may incorporate cyanine dye deoxyuridine analogs (Yu et al., *Nucleic Acids Res.*, 22:3226–3232 (1994)) at a frequency of 4 analogs for every 100 nucleotides. A preferred method for detecting nucleic acid amplified in situ is to label the DNA during amplification with BrdUrd, followed by binding of the incorporated BrdU with a biotinylated anti-BrdU antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.). Other methods for detecting nucleic acid amplified in situ include labeling the DNA during amplification with 5-methylcytosine, followed by binding of the incorporated 5-methylcytosine with an antibody (Sano et al., *Biochim. Biophys. Acta* 951:157–165 (1988)), or labeling the DNA during amplification with aminoallyl-deoxyuridine, followed by binding of the incorporated aminoallyl-deoxyuridine with an Oregon Green® dye (Molecular Probes, Eugene, Oreg.) (Henegariu et al., *Nature Biotechnology* 18:345–348 (2000)).

Another method of labeling amplified nucleic acids is to incorporate 5-(3-aminoallyl)-dUTP (AAdUTP) in the nucleic acid during amplification followed by chemical labeling at the incorporated nucleotides. Incorporated 5-(3-aminoallyl)-deoxyuridine (AAdU) can be coupled to labels that have reactive groups that are capable of reacting with amine groups. AAdUTP can be prepared according to Langer et al. (1981). Proc. Natl. Acad. Sci. USA. 78: 6633–37. Other modified nucleotides can be used in analogous ways. That is, other modified nucleotides with minimal modification can be incorporated during replication and labeled after incorporation.

Examples of labels suitable for addition to AAdUTP are radioactive isotopes, fluorescent molecules, phosphorescent molecules, enzymes, antibodies, and ligands. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamnine, xanthenes, acridines, oxazines, phycoerythrin, macrocyclic chelates of lanthanide ions such as quantum dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodarine WT, Serotonin, Sevron Brilliant Red 2B, Sevron Brilliant Red 4G, Sevron Brilliant Red B, Sevron Orange, Sevron. Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

ii. Secondary Labeling with Detection Probes

Secondary labeling consists of using suitable molecular probes, referred to as detection probes, to detect the amplified nucleic acids. For example, a primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand.

iii. Multiplexing and Hybridization Array Detection

Detection of amplified nucleic acids can be multiplexed by using sets of different primers, each set designed for amplifying different target sequences. Only those primers that are able to find their targets will give rise to amplified products. There are two alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the target sequence as an address tag.

iv. Enzyme-linked Detection

Amplified nucleic acid labeled by incorporation of labeled nucleotides can be detected with established enzyme-linked detection systems. For example, amplified nucleic acid labeled by incorporation of biotin using biotin-16-UTP (Roche Molecular Biochemicals) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

2. Linear Strand Displacement Amplification

A modified form of multiple strand displacement amplification can be performed which results in linear amplification of a target sequence. This modified method is referred to as linear strand displacement amplification (LSDA) and is accomplished by using a set of primers where all of the primers are complementary to the same strand of the target sequence. In LSDA, as in MSDA, the set of primers hybridize to the target sequence and strand displacement amplification takes place. However, only one of the strands of the target sequence is replicated. LSDA requires thermal cycling between each round of replication to allow a new set of primers to hybridize to the target sequence. Such thermal cycling is similar to that used in PCR. Unlike linear, or single primer, PCR, however, each round of replication in LSDA results in multiple copies of the target sequence. One copy is made for each primer used. Thus, if 20 primers are used in LSDA, 20 copies of the target sequence will be made in each cycle of replication.

DNA amplified using MSDA and WGSDA can be further amplified by transcription. For this purpose, promoter sequences can be included in the non-complementary portion of primers used for strand displacement amplification, or in linker sequences used to concatenate DNA for MSDA-CD.

3. Reverse Transcription Multiple Displacement Amplification

Multiple displacement amplification can be performed on RNA or on DNA strands reverse transcribed from RNA. A useful form of the disclosed method, referred to as reverse transcription multiple displacement amplification (RT-MDA) involves reverse transcribing RNA, removal of the RNA (preferably by nuclease disgestion using an RNA-specific nuclease such as RNAse H), and multiple displacement amplification of the reverse transcribed DNA. RT-MDA can be performed using either double-stranded cDNA or using just the first cDNA strand. In the latter case, the second cDNA strand need not be, and preferably is not, synthesized. RT-MDA is useful for quantitative analysis of mRNA or general amplification of mRNA sequences for any other purpose.

4. Repeat Multiple Displacement Amplification

The disclosed multiple displacement amplification operations can also be sequentially combined. For example, the product of NDA can itself be amplified in another multiple displacement amplification. This is referred to herein as repeat multiple displacement amplification (RMDA). This can be accomplished, for example, by diluting the replicated strands following MDA and subjecting them to a new MDA. This can be repeated one or more times. Each round of MDA will increase the amplification. Different forms of MDA, such as WGSDA and MSDA on particular target sequences can be combined. In general, repeat MDA can be accomplished by first bringing into contact a set of primers, DNA polymerase, and a target sample, and incubating the target sample under conditions that promote replication of the target sequence. Replication of the target sequence results in replicated strands, wherein during replication at least one of the replicated strands is displaced from the target sequence by strand displacement replication of another replicated strand; and then diluting the replicated strands, bringing into contact a set of primers, DNA polymerase, and the diluted replicated strands, and incubating the replicated strands under conditions that promote replication of the target sequence. Replication of the target sequence results in additional replicated strands, wherein during replication at least one of the additional replicated strands is displaced from the target sequence by strand displacement replication of another additional replicated strand. This form of the method can be extended by performing the following operation one or more times: diluting the additional replicated strands, bringing into contact a set of primers, DNA polymerase, and the diluted replicated strands, and incubating the replicated strands under conditions that promote replication of the target sequence. Replication of the target sequence results in additional replicated strands, wherein during replication at least one of the additional replicated strands is displaced from the target sequence by strand displacement replication of another additional replicated strand.

5. Using Products of Multiple Displacement Amplification

The nucleic acids produced using the disclosed method can be used for any purpose. For example, the amplified nucleic acids can be analyzed (such as by sequencing or probe hybridization) to determine characteristics of the amplified sequences or the presence or absence or certain sequences. The amplified nucleic acids can also be used as reagents for assays or other methods. For example, nucleic acids produced in the disclosed method can be coupled or adhered to a solid-state substrate. The resulting immobilized nucleic acids can be used as probes or indexes of sequences in a sample. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

Nucleic acids produced in the disclosed method also can be used as probes or hybridization partners. For example, sequences of interest can be amplified in the disclosed method and provide a ready source of probes. The replicated strands (produced in the disclosed method) can be cleaved prior to use as hybridization probes. For example, the replicated strands can be cleaved with DNAse I. The hybridization probes can be labeled as described elsewhere herein with respect to labeling of nucleic acids produce in the disclosed method.

Nucleic acids produced in the disclosed method also can be used for subtractive hybridization to identify sequences that are present in only one of a pair or set of samples. For example, amplified cDNA from different samples can be annealed and the resulting double-stranded material can be separated from single-stranded material. Unhybridized sequences would be indicative of sequences expressed in one of the samples but not others.

EXAMPLES

E. Example 1

Whole Genome Amplification Using Nuclease Resistant Hexamer Primers

This example describes a demonstration of an embodiment of the disclosed method and analysis and comparison of the results. The exemplified method is the disclosed multiple displacement amplification form of whole genome amplification using nuclease resistant random hexamer primers. Some reactions in this example were performed without subjecting the sample to denaturing conditions, a preferred form of the disclosed method. In other reactions, the template DNA was subjected to denaturation prior to amplification. MDA was performed using φ29 DNA polymerase.

1. Materials and Methods i. DNA and Enzymes.

A panel of human genomic DNA samples, the Human Variation Panel-Caucasian Panel of 100 (reference number HD 100CAU) was obtained from Coriell Cell Repositories. Human genomic DNA was also obtained from Promega Corp. Thiophosphate-modified random hexamer (5'-NpNpNpNp$^s$Np$^s$N-3') was synthesized at Molecular Staging, φ29 DNA polymerase was from Amersham Pharmacia Biotech, and yeast pyrophosphatase was from Boehringer-Mannheim. DNA size markers (100 bp DNA ladder, 1Kb DNA ladder) were from Gibco BRL.

ii. Amplification of Human Genomic DNA.

Human genomic DNA (300 ng to 0.03 ng, as indicated) was placed into 0.2 ml tubes in a total volume of 50 μl, yielding final concentrations of 25 mM Tris-HCl, pH 7.5, 50 mM KCl, 10 mM MgCl$_2$, and 100 μM exonuclease-resistant hexamer. A heat-treatment step (that is, exposure to denaturing conditions) to increase primer annealing was included or omitted, as indicated, for individual experiments. Annealing reactions were heated to 95° C. for 3 minutes and chilled to 4° C. in a PCR System Thermocycler (Perkin Elmer). Reactions were then brought to a final volume of 100 μl, containing final concentrations of 37 mM Tris-HCl, pH 8.0, 50 mM KCl, 10 mM MgCl$_2$, 5 mM (NH$_4$)$_2$SO$_4$, 1.0 mM dNTPs, 1 unit/ml of yeast pyrophosphatase, 50 μM exonuclease-resistant hexamer, and 800 units/ml φ29 DNA polymerase. Radioactively labeled α-[$^{32}$P] dCTP, approximately 60 cpm/pmol total dNTPs, was added as indicated. Reactions were incubated for 18 hours at 30° C. Incorporation of acid-precipitable radioactive deoxyribonucleotide product was determined with glass fiber filters. After the reactions were terminated, 3 μl aliquots were cleaved with restriction endonuclease AluI and analyzed by electrophoresis through a 1.0% agarose gel in Tris-borate-EDTA buffer, stained with GelStar (Molecular Probes) or SYBR Green (Molecular Probes), and imaged with a Storm 860 PhosphorImager (APB). Denaturing gel analysis was carried out by electrophoresis through a 1.0% agarose gel in 30 mM NaOH, 1 mM EDTA. The radioactive products in the dried gel were visualized with the Storm 860 PhosphorImager.

iii. Southern Analysis.

10 μg of whole genome amplified DNA or human genomic DNA controls were digested with EcoRI restriction endonuclease and separated through a 1% agarose gel in 1×TBE buffer. Standard Southern analysis procedure (Southern, Detection of specific sequences among DNA fragments separated by gel electrophoresis. *J Mol Biol.* 98:503–517 (1975)) was performed using a Hybond-N+ membrane (Amersham Pharmacia Biotech, Piscataway, N.J.). An exon fragment probe of parathyroid hormone (p20.36) and RFLP marker probes for the D13S12 (p9D11) and Thyroglobulin (pCHT.16/8) loci were obtained from American Type Culture Collection. Probes were radiolabeled using the NEBlot random primer labeling method (New England Biolabs, Beverly, Mass.). The membrane was prehybridized for 1 hr and hybridized to the radiolabeled probe overnight in a Membrane Hybridization Buffer (Amersham Pharmacia Biotech, Piscataway, N.J.). The hybridized membrane was washed in 2×SSC and 0.1% SDS twice for 5 min at room temperature, 1×SSC and 0.1%SDS for 15 min at 42° C., and 0.1×SSC twice for 15 min at 65° C. The membrane was then exposed overnight and analyzed using the Storm 860 PhosphorImager.

iv. Quantitative PCR Analysis.

TaqMan analysis was performed using the ABI 7700 according to the manufacturer's specifications (Applied Biosystems, Foster City, Calif.) using 1 μg of amplified DNA as template. TaqMan assay reagents for the 8 loci tested were obtained from ABI. The 8 loci and their chromosome assignments were, acidic ribosomal protein (1p36.13); connexin 40 (1q21.1); chemokine (C-C motif) receptor 1 (3p21); chemokine (C-C motif) receptor 6 (6q27); chemokine (C-C) receptor 7 (17q21); CXCR5 Burkitt lymphoma receptor 1 (chr. 11); c-Jun (1p32-p31); and MKP1 dual specificity phosphatase 1 (5q34). Connexin 40 is located near the centromere and chemokine (C-C motif) receptor 6 is located near the telomere. A standard curve for input template was generated to determine the loci copy number in amplified DNA relative to that of genomic DNA. The standard curve was generated from 0, 0.001, 0.01, 0.1, 0.5, and 1 μg of genomic DNA.

v. Amplification of Human Genomic DNA by Degenerate Oligonucleotide PCR (DOP-PCR).

Human genomic DNA (ranging from 300 ng to 0.03 ng) was amplified as described (Telenius et al., *Genomics.* 13:718–725 (1992)). Radioactively labeled α-[$^{32}$P] dCTP, approximately 60 cpm/pmol total dNTPs, was added to the reaction for the quantitation of PCR product yield. Taq DNA Polymerase was from Invitrogen Life Technologies, Carlsbad, Calif. DOP-PCR amplifications were carried out using a GeneAmp 9700 PCR System thermocycler (Applied Biosystems, Foster City, Calif.). Locus representation in the DOP-PCR product was quantitatively analysed using the TaqMan assay (Invitrogen Life Technologies, Carlsbad, Calif.).

vi. Amplification of Human Genomic DNA by Primer Extension Preamplification (PEP).

Human genomic DNA (ranging from 300 ng to 0.03 ng) was placed into 0.2 ml tubes in a total volume of 60 μl, yielding final concentrations of 33 μM PEP random primer (5'-NNN NNN NNN NNN NNN-3') as described (Zhang et al., Whole genome amplification from a single cell: implications for genetic analysis. *Proc Natl Acad Sci U S A.* 89:5847–5851 (1992)). Radioactively labeled α-[$^{32}$P] dCTP, approximately 60 cpm/pmol total dNTPs, was added to the reaction for the quantitation of PCR product. PEP reactions were carried out using a GeneAmp 9700 PCR System thermocycler (Applied Biosystems, Foster City, Calif.). Locus representation in the PEP product was quantitatively analysed using the TaqMan assay (Invitrogen Life Technologies, Carlsbad, Calif.).

vii. Genotyping of Single Nucleotide Polymorphisms.

The SNPs analyzed here had the following chromosomal locations; 1822, 251, and 221, 13q32; 465, 458, and 474, 19q13; VCAM, 1p31; IL-8, 4q13; PDK2-2, 17p; SNP21, not known. Assays were carried out as described by Faruqi et al., High-Throughput Genotyping of Single Nucleotide Polymorphisms with Rolling Circle Amplification. *BMC Genomics,* 2:4 (2001). Briefly, DNA denaturation, annealing and ligation reactions were carried out in an Eppendorf Master Cycler (Eppendorf Scientific, Germany). Exponential RCA reactions were performed in the Real-Time ABI 7700 Sequence Detector (Perkin Elmer). Two controls lacking ligase were also carried out for each SNP, confirming the specificity of the assays. The DNA samples were digested with the restriction endonuclease AluI before being used as template in the ligation reaction. Ligation reactions were set up in 96-well MicroAmp Optical plates (Perkin Elmer) in a 10 μl reaction volume containing 1 unit Ampligase (Epicentre Technologies), 20 mM Tris-HCl (pH 8.3), 25 mM KCl, 10 mM $MgCl_2$, 0.5 mM NAD, and 0.01% Triton® X-100. Standard reactions contained 0.5 pM open circle padlock and 100 ng of Alu I digested genomic DNA. DNA was denatured by heating the reactions at 95° C. for 3 min followed by annealing and ligation at 60° C. for 20 min. 20 μl of ERCA mix was added to the 10 μl ligation reaction. The ERCA mix contained 5% TMA oxalate, 400 μM dNTP mix, 1 μM each of the two primers, 8 units of Bst polymerase (New England Biolabs, Mass.), and 1× modified ThermoPol II reaction buffer containing 20 mM Tris-HCl (pH 8.8), 10 mM KCl, 10 mM $(NH_4)_2SO_4$ and 0.1% Triton® X-100.

viii. Comparative Genome Hybridization.

Genomic DNA preparations were nick-translated to incorporate nucleotides modified with biotin for amplified samples or digoxigenin for unamplified control samples. Equimolar amounts of amplified and unamplified DNA were co-hybridized in the presence or absence of CotI DNA to suppress repetitive DNA cross-hybridization. Specific hybridization signals were detected by avidin-FITC and anti-digoxigenin rhodamine. Captured images of metaphase chromosomes were analyzed using the Applied Imaging CGH software program and fluorescence profiles were generated. As controls, differentially labeled amplified or unamplified DNAs were mixed, hybridized, detected and subjected to ratio analysis as outlined above.

2. Results

Using the embodiment of the disclosed method, 30 pg (approximately 9 genomic copies) of human genomic DNA was amplified to approximately 30 μg within 4 hours. The average fragment length was greater than 10 kb. The amplified human DNA exhibited normal representation for 10 single nucleotide polymorphisms (SNPs). Maximum bias among 8 chromosomal loci was less than 3-fold in contrast to four to six orders of magnitude for PCR-based WGA methods. Human DNA amplified with the disclosed method is useful for several common methods of genetic analysis, including genotyping of single nucleotide polymorphisms (SNP), chromosome painting, Southern blotting and RFLP analysis, subcloning, and DNA sequencing.

It has been discovered that the use of random hexamer primers and ϕ29 DNA polymerase in multiple displacement amplification, a cascading, strand displacement reaction (U.S. Pat. No. 6,124,120 to Lizardi), will readily amplify linear, human genomic DNA. Amplification of genomic DNA by the disclosed form of MDA at 30° C. is exponential for 4–6 hours. The effect of template concentration on amplification yield in the disclosed method is shown in FIG. 1. 100 fg to 10 ng human genomic DNA was denatured at 95° C. for 5 min, and then MDA was carried out at 30° C. as described above. Aliquots were taken at the times indicated in FIG. 1 to quantitate DNA synthesis. Amplification reactions (100 μl) yielded approximately 25–30 μg DNA product regardless of the starting amount of genomic DNA over a 5-log range (100 fg to 10 ng; FIG. 1). For some applications, this allows subsequent genetic analysis without the need to measure or adjust DNA concentration.

The products of the MDA reaction were characterized as follows. Radioactively labeled human genome amplification samples (0.6 μg) were electrophoresed through an alkaline agarose gel (1%, Tris-Borate EDTA buffer), stained, and imaged as described above. Average product length exceeded 10 kb.

To examine the integrity of amplified DNA, a restriction fragment within the human parathyroid hormone gene (chromosome 11p15.2-15.1) was analyzed on Southern blots. A 1.9 kb restriction enzyme fragment was observed for MDA-based WGA products amplified from as few as 10 genomic copies (or $10^6$-fold amplification). These MDA reactions included a heat denaturation step and amplification was carried out as described above. EcoRI DNA digests were probed using a radioactively-labeled genomic fragment of the parathyroid hormone gene (p20.36) that hybridized to an approximately 1.9 kb DNA fragment. The EcoRI-cleaved DNA preparations were genomic DNA, DNA amplified by MDA from varying amounts of input genomic DNA, or an MDA reaction that lacked input genomic DNA template. This demonstrates that the products of MDA are long enough to yield specific DNA fragments several kb in length after cleavage by restriction endonucleases.

While PCR-based WGA methods typically generate products of only several hundred nucleotides in length (Telenius et al., Genomics. 13:718–725 (1992); Cheung and Nelson, Proc Natl Acad Sci USA. 93:14676–14679 (1996); Zhang et al., Proc Natl Acad Sci USA. 89:5847–5851 (1992)), products of the disclosed method were of sufficient length and integrity for RFLP-based genotyping: 16 random individuals were correctly genotyped by the presence of a 2.1 kb, and 1.1 kb Pst I fragment. Specifically, PstI DNA digests were probed using a radioactively-labeled genomic fragment of the RFLP marker D13S12 locus (p9D11) that hybridized to an invariant 3.8 kb DNA fragment and a polymorphic 2.1 kb (allele A) or 1.1 kb (allele B) DNA fragment. The PstI-cleaved DNA preparations were genomic DNA and 5 different patient DNAs amplified by MDA without any heat denaturation of the DNA template (10,000× amplification).

Omission of denaturation conditions prior to MDA was useful for detection of restriction fragments greater than 5 kb in length. MDA reactions were performed with or without heat denaturation of the genomic target DNA heterozygous for two thyroglobulin alleles. Amplification was carried out as described above. TaqI DNA digests were probed using a radioactively-labeled genomic fragment of the thyroglobulin gene (pCHT. 16/8) that hybridized to invariant 1 kb and 3 kb DNA fragments and a polymorphic 5.8 kb (allele A) or 5.2 kb (allele B) DNA fragment. The TaqI-cleaved DNA preparations were genomic DNA, DNA amplified by MDA reaction (10,000×) with a 95° C. preheating step, and an MDA reaction (10,000×) without the preheating step. MDA without heat denaturation gave a good yield of DNA fragments 5.2 and 5.8 kb in size, while neither of the 5.2 or 5.8 kb DNA fragments were visible using MDA with heat denaturation of the template.

The most useful results from whole geneome amplification are obtained when the amplification provides complete coverage of genomic sequences and minimal amplification bias. It is also preferred that the amplification product perform similarly to unamplified genomic DNA during subsequent genetic analysis. Genome coverage after MDA with heat denaturation of the template was examined for 10 randomly distributed SNPs after amplifications of 100-, 10,000-, or 100,000-fold. The presence of all loci was confirmed in the amplified DNA with the exception of one locus (PDK2-2) in 100,000-fold amplified DNA (Table 1). MDA DNA from 72 individuals was genotyped for one of these SNPs. Following 100-fold amplification by MDA, genotyping accuracy was 97% (70 of 72 genotypes scored correctly, Table 1, SNP 1822), a result that was indistinguishable from unamplified genomic DNA genotyped by the same method. MDA-based WGA thus offers an attractive alternative to multiple locus-specific PCR preamplifications for large SNP scoring studies, especially where sample availability is limited.

TABLE 1

| | Fold whole genome amplification | | |
|---|---|---|---|
| SNP designation | 100× | 10,000× | 100,000× |
| | Correct SNP calls/total assays | | |
| 1822 | 70/72 | 4/4 | 3/4 |
| 251 | 8/8 | 4/4 | 4/4 |
| 221 | 3/4 | 3/4 | 4/4 |
| 465 | 4/4 | 3/4 | 3/4 |
| 458 | 4/4 | 3/4 | 3/4 |
| 474 | 4/4 | 3/4 | 4/4 |
| VCAM | 4/4 | 4/4 | 4/4 |
| IL-8 | 4/4 | 4/4 | 3/4 |
| SNP21 | 4/4 | 4/4 | 3/4 |
| PDK2-2 | 4/4 | 4/4 | 0/12 |

Sequence bias can occur in amplification methods, and may result from factors such as priming efficiency, template accessibility, GC content, and proximity to telomeres and centromeres. Amplification bias of the disclosed MDA method was examined by TaqMan quantitative PCR for 8 genes, including one near the centromere of chromosome 1 (connexin 40) and one adjacent to the telomere of chromosome 6 (chemokine (C-C motif) receptor 6). For 100, 1,000, and 10,000-fold MDA without heat denaturation, the maximum amplification biases were only 2.7, 2.3, and 2.8 respectively, expressed as the ratio of the most highly represented gene to the least represented gene. In contrast, two WGA methods based on PCR, DOP-PCR (Telenius et al., *Genomics*. 13:718–725 (1992); Cheung and Nelson, *Proc Natl Acad Sci USA*. 93:14676–14679 (1996)) and PEP (Zhang et al., *Proc Natl Acad Sci USA*. 89:5847–5851 (1992)), exhibited amplification bias of 4–6 orders of magnitude. These values were consistent with literature values for the bias of PCR-mediated WGA methods; PEP has been reported to generate an amplification bias of up to 50-fold even between two alleles of the same gene (Paunio et al., *Clin. Chem.* 42:1382–1390 (1996)). Significantly, the 3-fold amplification bias of MDA remained almost constant between 100 and 100,000-fold amplification. An absence of significant sequence bias observed in MDA-based WGA may be explained by the extraordinary processivity of $\phi 29$ DNA polymerase (Blanco et al., *J. Biol. Chem.* 264:8935–8940 (1989)). Tight binding of the polymerase to the template assures replication through obstacles caused by DNA primary or secondary structure.

Surprisingly, TaqMan quantification indicated that certain gene loci were enriched by MDA in amplified DNA; locus representation was >100% of the representation in genomic DNA. Representation of mitochondrial DNA was the same between starting gDNA and amplified DNA. Southern blots and chromosome painting experiments indicated that repetitive sequences were underrepresented in MDA product, conferring an effective enrichment of genes. Thus, amplified DNA contained between 100–300% copy numbers of 8 genes relative to genomic DNA. Additional studies will be necessary to identify the extent and type of repetitive element under-representation; one hypothesis for this observation is that primers corresponding to highly repetitive elements become depleted during MDA. However, in contrast to PCR-based WGA products, which contain up to 70% amplification artifacts (Cheunng and Nelson, Whole genome amplification using a degenerate oligonucleotide primer allows hundreds of genotypes to be performed on less than one nanogram of genomic DNA. *Proc Natl Acad Sci USA*. 93:14676–14679 (1996)), MDA-based WGA products appear to be entirely derived from genomic sequences.

Whole genome MDA was also tested for uniformity of chromosome coverage by comparative genomic hybridization. MDA-generated DNA was cohybridized to metaphase chromosomes with an equivalent amount of unamplified genomic DNA. Amplification reactions included a heat denaturation step and amplification was carried out as described above. Amplified and unamplified DNA samples were nick-translated to incorporate biotin nucleotide and digoxigenin nucleotide, respectively. Specific signals were detected by avidin FITC and anti-digoxigenin rhodamine. With CotI suppression, the hybridization patterns of MDA probes and unamplified probes were indistinguishable even after 100,000-fold amplification. Without CotI suppression, however, the 100,000-fold amplified probe gave reduced centromeric signals, indicating some loss of repetitive centromeric sequences. The uniformity of signal along the length of the chromosome arms was further evidence that MDA-based WGA does not induce significant amplification bias. These results indicated that MDA compared favorably with DOP PCR for preparation of chromosome painting probes (Kim et al., Whole genome amplification and molecular genetic analysis of DNA from paraffin-embedded prostate adenocarcinoma tumor tissue. *J Urol.* 162:1512–1518 (1999); Klein et al., Comparative genomic hybridization, loss of heterozygosity, and DNA sequence analysis of single cells. *Proc Natl Acad Sci USA* 96:4494–4499 (1999); Wells et al., Detailed chromosomal and molecular genetic analysis of single cells by whole genome amplification and comparative genomic hybridization. *Nucleic Acids Res* 27:1214–1218 (1999)), but that unlike the latter, suppression hybridization may be unnecessary for detection of single copy sequences. This method should be invaluable for DNA probe preparation for comparative genome hybridization, karyotyping and chip-based genetic analysis from limited patient DNA sources such as needle biopsy material or amniocentesis samples.

For genome subcloning and sequencing MDA appears to have several intrinsic advantages over PCR-based methods. Product size of >10 kb is compatible with genome subcloning. Since no in vivo propagation of amplified material is necessary, MDA may represent an efficient method for amplifying "poisonous" genomic sequences. In addition, $\phi 29$ DNA polymerase used for MDA has an error rate of 1 in $10^6$–$10^7$ (Esteban et al., Fidelity of Phi29 DNA polymerase. Comparison between protein-primed initiation and DNA polymerization. *J. Biol. Chem.* 268:2719–2726 (1993)) in contrast to approximately 3 in $10^4$ for PCR with Taq DNA polymerase (Eckert and Kunkel, DNA polymerase fidelity and the polymerase chain reaction. *PCR Methods and Applications.* 1:17–24 (1991)). Therefore, PCR accumulates about one mutation per 900 bases (Saiki et al., Primer-directed enzymatic amplification of DNA with a thermostable DNA polymerase. *Science* 239:487–491 (1988)) after 20 cycles. Sequence error rates of cloned MDA-based WGA products appear to be similar to those for cloned genomic DNA. Furthermore, minimal amplification bias, uniform yields, and assay simplicity make MDA amenable to the automated, high-density microwell formats used for genome subcloning and sequencing.

In summary, the utility of MDA-based WGA was demonstrated for a variety of uses including quantitative PCR, SNP genotyping, Southern blot analysis of restriction fragments, and chromosome painting. Several situations may be contemplated where MDA may represent the method of choice for WGA: Firstly, applications where faithful replication during WGA is necessary, such as molecular cloning, or single cell analysis; Secondly, applications where adequate genome representation during WGA is critical, such as genome-wide SNP genotyping studies; And thirdly, where minimization of bias during WGA is important, particularly cytogenetic testing such as pre-natal diagnosis (Harper and Wells, Recent advances and future developments in PGD. *Prenat Diagn.* 19:1193–1199 (1999)), comparative genome hybridization (Wells and Delhanty, Comprehensive chromosomal analysis of human preimplantation embryos using whole genome amplification and single cell comparative genomic hybridization. *Mol Hum Reprod.* 6:1055–1062 (2000)), and assessment of loss of heterozygosity (Paulson et al., Loss of heterozygosity analysis using whole genome amplification, cell sorting, and fluorescence-based PCR. *Genome Res.* 9:482–491 (1999)). Additional situations where there is a significant need for WGA include amplification of DNA from micro-dissected tissues (Kim et al., Whole genome amplification and molecular genetic analysis of DNA from paraffin-embedded prostate adenocarcinoma tumor tissue. *J Urol.* 162:1512–1518 (1999)), buccal smears (Gillespie et al., HLA class II typing of whole genome amplified mouth swab DNA. *Tissue Antigens.* 56:530–538 (2000)), and archival, anthropological samples (Buchanan et al., Long DOP-PCR of rare archival anthropological samples. *Hum Biol.* 72:911–925 (2000)). Finally, DNA amplified from sorted, individual chromosomes may be used for the generation of whole chromosome-specific painting probes (Guillier-Gencik et al., Generation of whole-chromosome painting probes specific to each chicken macrochromosome. *Cytogenet Cell Genet.* 87:282–285 (1999)).

F. Example 2

Increasing Time of Incubation at 95° C. Causes Increasing Template DNA Strand Breakage This example demonstrates that significant template DNA strand breakage is generated by incubation at 95° C. (which is used in typical amplification reactions to denature the DNA), and that strand breakage is reduced by decreasing the duration of heat treatment. As with most nucleic acid amplification techniques, the integrity of the starting DNA template can have an important effect on the rate and yield of the amplified product. In reactions where the nucleic acid to be amplified is degraded, the yield of amplified product may be reduced both in quality and quantity. This example demonstrates the reduction of template DNA strand breakage by decreasing time of incubation at 95° C.

Figure 2:
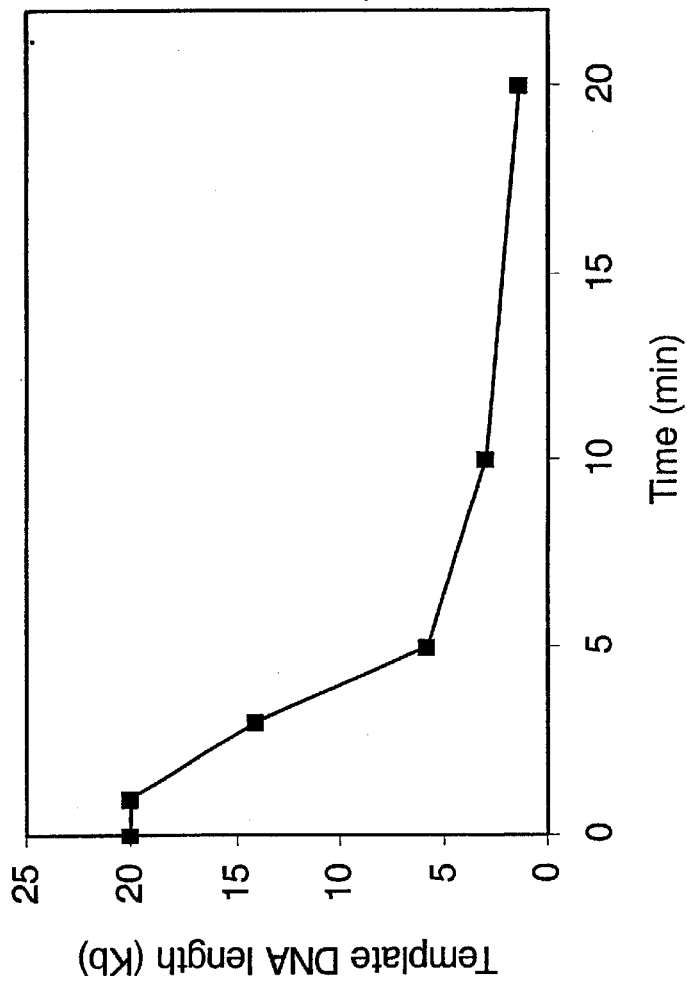
FIG. 2 is a graph of the effect of incubation time at 95° C. on template DNA length.

Six reactions were carried out under the conditions used for DNA template strand separation with heat-denaturation in order to illustrate the degradation of template DNA. Human genomic DNA (10 μg) was placed into a 0.2 ml tube in a total volume of 50 μl, yielding final concentrations of 25 mM Tris-HCl, pH 7.5, 50 mM KCl, 10 mM $MgCl_2$. Reactions were heated to 95° C. in a PCR System Thermocycler (Perkin Elmer), and an aliquot of 8 μl was taken and put on ice at indicated times. For each time point, a 2 μl aliquot was analyzed by electrophoresis through a 0.8% alkaline agarose gel (30 mM NaOH, 1 mM EDTA). After electrophoresis, the gel was neutralized with 1×TBE, stained with SYBR Green II (Molecular Probes), and imaged with a Storm 860 PhosphorImager (APB). The total amount of DNA imaged was determined for each lane of the gel and the fragment size at which 50% of the DNA was larger, and 50% was smaller, was determined for the samples drawn at each time point. The results are shown in FIG. 2.

As can be seen, significant breakage of template DNA occurs after incubation at 95° C. for longer than three minutes. Such DNA breakage is substantially reduced when incubation is limited to one minute.

G. Example 3

Increasing Time of DNA Template Incubation at 95° C. Causes Decreased Rate and Yield of DNA Amplification This example demonstrates that increased time of template DNA incubation at 95° C. (which is used in typical amplification reactions to denature the DNA) causes a reduction in both the rate and the yield with which DNA is amplified by MDA. Omission of DNA template incubation at 95° C. results in the greatest rate and yield of DNA amplification.

Figure 3:
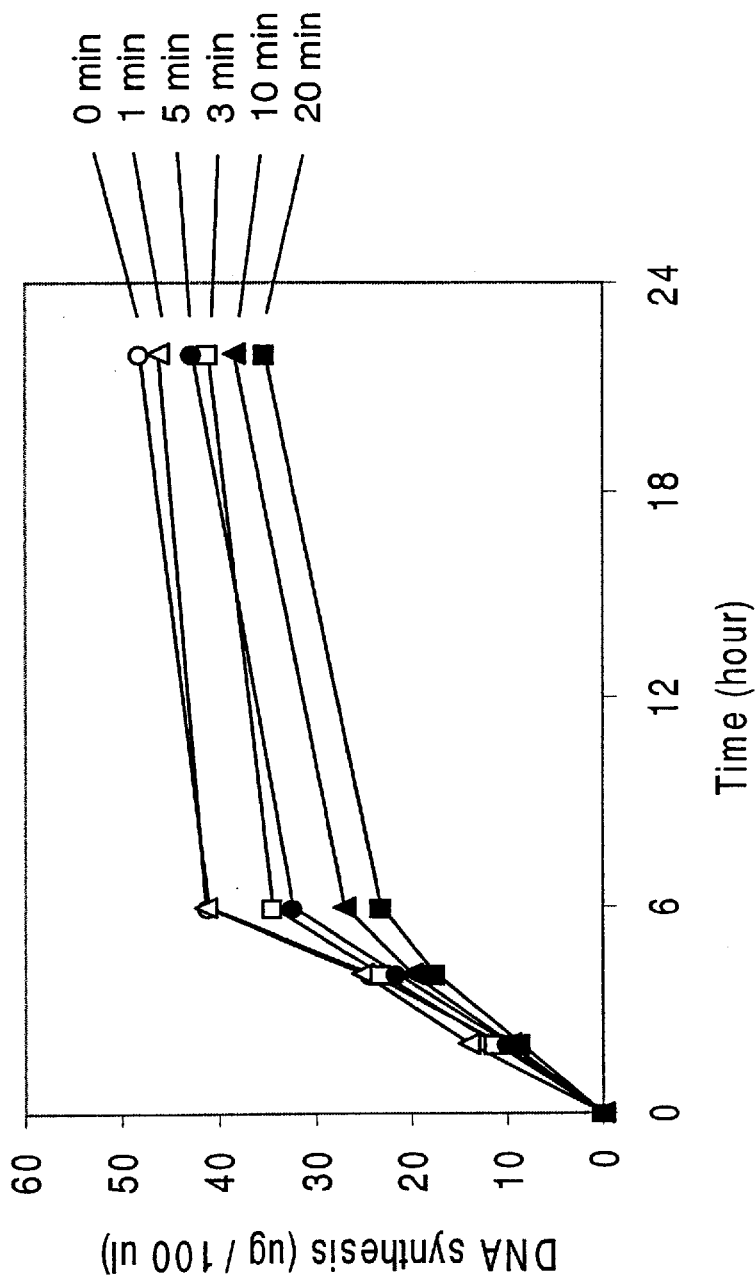
FIG. 3 is a graph of the effect of template incubation at 95° C. on the rate and yield of MDA.

Six MDA reactions were carried out using template DNA treated at 95° C. under the conditions described in Example 2. Purified human genomic DNA (3 ng) was placed into 0.2 ml tubes in a total volume of 50 μl, containing 25 mM Tris-HCl, pH 7.5, 50 mM KCl, and 10 mM $MgCl_2$. Reactions were heated to 95° C. for the time indicated and chilled to 4° C. in a PCR System Thermocycler (Perkin Elmer). These reactions were then brought to a final volume of 100 μl, containing final concentrations of 37 mM Tris-HCl, pH 7.5, 50 mM KCl, 10 nM $MgCl_2$, 50 μM exonuclease-resistant hexamer, 5 mM $(NH_4)_2SO_4$, 1.0 mM dNTPs, 1 unit/ml of yeast pyrophosphatase, and 800 units/ml φ29 DNA polymerase. Radioactively labeled α-[$^{32}$P] dCTP, approximately 60 cpm/pmol total dNTPs, was added and reactions were incubated for 22 hours at 30° C. Aliquots were taken at the times indicated and incorporation of acid-precipitable radioactive deoxyribonucleotide product was determined with glass fiber filters. The results are shown in FIG. 3.

As can be seen, omission of heat treatment of the DNA template results in the optimal rate and yield of DNA synthesis (see 0 min curve). Increasing duration of DNA template heat treatment resulted in progressively reduced rate and yield of DNA synthesis (see 1 min, 3 min, 5 min, 10 min, and 20 min curves).

H. Example 4

Increasing Time of DNA Template Incubation at 95° C. Results in Decreasing DNA Product Strand Size This example demonstrates that increased time of template DNA incubation at 95° C. (which is used in typical amplification reactions to denature the DNA) causes a reduction in the length of the DNA products amplified by MDA. Omission of DNA template incubation at 95° C. results in the greatest size of DNA amplification products.

Figure 4:
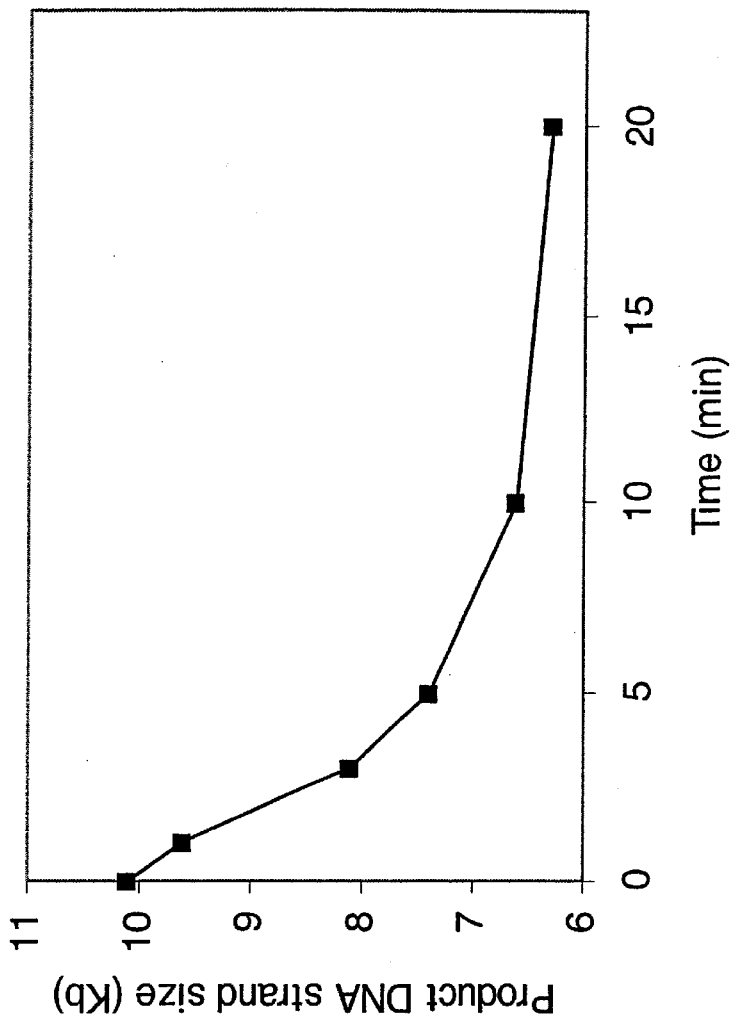
FIG. 4 is a graph of the effect of template incubation at 95° C. on the average size of DNA product strands.

Six MDA reactions were carried out using template DNA treated at 95° C. under the conditions described in Example 3. Radioactively labeled α-[$^{32}$P] dCTP was added, approximately 60 cpm/pmol total dNTPs. Reactions were incubated for 22 hours at 30° C. and aliquots were taken at the times indicated. For each time point, a 2 μl aliquot was analyzed by electrophoresis through a 0.8% alkaline agarose gel (30 mM NaOH, 1 mM EDTA). After electrophoresis, the gel was neutralized and imaged as described in Example 2. The total amount of DNA imaged was determined for each lane of the gel and the fragment size at which 50% of the DNA was larger, and 50% was smaller, was determined for the samples from each time point. The results are shown in FIG. 4.

As can be seen, omission of heat treatment of the DNA template results in the synthesis of the largest DNA products. Increasing duration of DNA template heat treatment resulted in progressively reduced DNA product size.

I. Example 5

Omission of DNA Template Incubation at 95° C. Results in Increased Locus Representation in DNA Products Amplified by MDA This example demonstrates that omission of template DNA incubation at 95° C. (which is used in typical amplification reactions to denature the DNA) results in no loss in the representation of eight randomly selected loci in DNA products amplified by MDA. Omission of DNA template incubation at 95° C. actually results in an increase in locus representation of DNA amplification products relative to template genomic DNA.

Two MDA reactions were carried out using template DNA either treated or not treated at 95° C. Purified human genomic DNA (3 ng) was placed into a 0.2 ml tube in a total volume of 50 μl, containing 25 mM Tris-HCl, pH 7.5, 50 mM KCl, 10 mM $MgCl_2$, and 100 μM exonuclease-resistant hexamer. The annealing reaction was heated to 95° C. for 3 minutes and chilled to 4° C. in a PCR System Thermocycler (Perkin Elmer). The reaction was then brought to a final volume of 100 μl, containing final concentrations of 37 mM Tris-HCl, pH 7.5, 50 mM KCl, 10 mM $MgCl_2$, 50 μM exonuclease-resistant hexamer, 5 mM $(NH_4)_2SO_4$, 1.0 mM dNTPs, 1 unit/ml of yeast pyrophosphatase, and 800 units/ml φ29 DNA polymerase. For amplification lacking the heat denaturation step, DNA template (3 ng) was placed directly into a 0.2 ml tube in a total volume of 100 μl containing 37 mM Tris-HCl, pH 7.5, 50 mM KCl, 10 mM $MgCl_2$, and 50 μM exonuclease-resistant hexamer, 5 mM $(NH_4)_2SO_4$, 1.0 mM dNTPs, 1 unit/ml of yeast pyrophosphatase, and 800 units/ml φ29 DNA polymerase. Reactions were incubated for 18 hours at 30° C.

Figure 5:
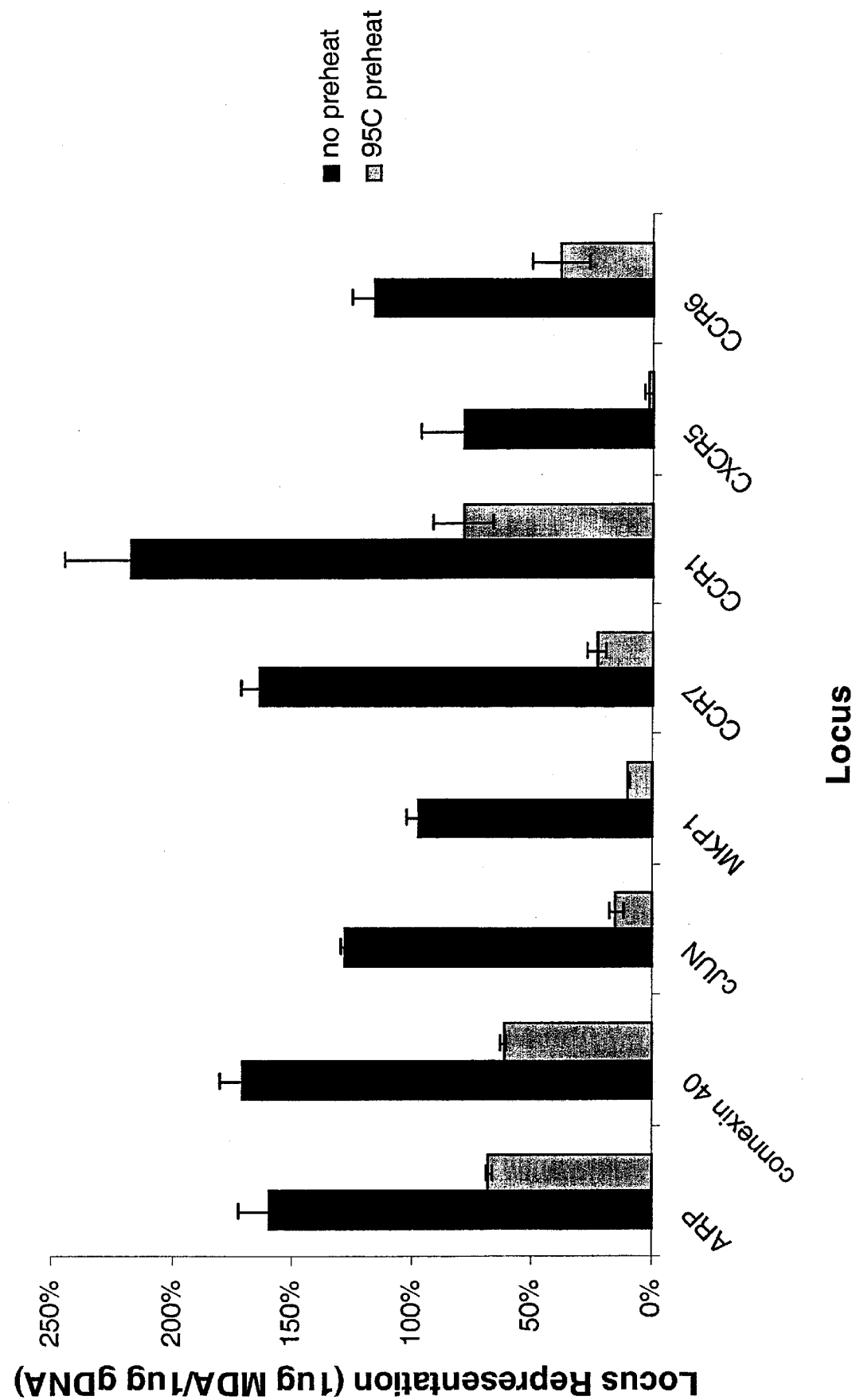
FIG. 5 is a graph showing a comparison of the effect of template incubation at 95° C. versus no incubation at 95° C. on locus representation in DNA amplified by MDA.

TaqMan® quantitative PCR analysis was performed using the ABI 7700 according to the manufacturer's specifications (Applied Biosystems, Foster City, Calif.) using 1 μg of MDA-amplified DNA as template. TaqMan® assay reagents for the 8 loci tested were obtained from ABI. The 8 loci and their chromosome assignments were, acidic ribosomal protein (1p36.13); connexin 40 (1q21.1); c-Jun (1p32-p31); MKP1 dual specificity phosphatase 1 (5q34); chemokine (C-C motif) receptor 7 (17q21); chemokine (C-C motif) receptor 1 (3p21); CXCR5 Burkitt lymphoma receptor 1 (chr. 11); and chemokine (C-C motif) receptor 6 (6q27). Connexin 40 is located near the centromere and chemokine (C-C motif) receptor 6 is located near the telomere. A standard curve for input template was generated to determine the loci copy number in amplified DNA relative to that of genomic DNA. The standard curve was generated from 0, 0.001, 0.01, 0.1, 0.5, and 1 μg of genomic DNA. The locus representation was expressed as a percent, relative to the locus representation in the input genomic DNA, and was calculated as the yield of quantitative PCR product from 1 μg amplified DNA divided by the yield from 1 μg genomic DNA control. The results are shown in FIG. 5.

As can be seen, there is no reduction of locus representation in DNA amplified from template DNA without heat treatment at 95° C. However, significant loss of locus representation was observed from template DNA heat-denatured for 3 min at 95° C.

J. Example 6

Amplification Bias of Loci Amplified by MDA is Significantly Lower than Amplification Bias of DNA Amplified by PEP or DOP-PCR This example demonstrates that, for 100-, 1,000-, and 10,000-fold MDA-amplified DNA, omission of template DNA incubation at 95° C. (which is used in typical amplification reactions to denature the DNA) results in low bias in the representation of eight randomly selected loci in DNA products. In contrast, two whole genome amplification (WGA) methods based on PCR, DOP-PCR and PEP, exhibit amplification biases of 2–6 orders of magnitude.

MDA reactions were carried out using template DNA not treated at 95° C. as described in Example 5. Reactions (100 μl) contained 300, 30, 3, or 0.3 ng DNA, resulting in approximately 100-, 1000-, 10,000-, and 100,000-fold DNA amplification.

Amplification of human genomic DNA by degenerate oligonucleotide PCR (DOP-PCR; Telenius et al., *Genomics.* 13:718–725 (1992); Cheung and Nelson, *Proc Natl Acad Sci USA.* 93:14676–14679 (1996)) was carried out as follows. Human genomic DNA (ranging from 300 ng to 0.03 ng) was placed into 0.2 ml tubes in a total volume of 50 μl, yielding final concentrations of 2 μM DOP Primer (5'-CCG ACT CGA GNN NNN NAT GTG G-3' (SEQ ID NO:20); N=A, G, C, or T in approximately equal proportions), 200 μM dNTPs, 10 mM Tris Cl (pH 8.3), 0.005% (v/v) BRIJ 35, 1.5 mM $MgCl_2$, and 50 mM KCl. Radioactively labeled α-$[^{32}P]$ dCTP, approximately 60 cpm/pmol total dNTPs was added to the reaction for quantitation of DNA synthesis as described for MDA product quantitation in Example 3. After the initial denaturation of the template at 95° C. for 5 min, 2.5 units Taq DNA Polymerase (Invitrogen Life Technologies, Carlsbad, Calif.) was added, followed by 5 cycles of 94° C. for 1 min, 30° C. for 1.5 min, ramping up to 72° C. in 3 min and elongation at 72° C. for 3 min, and then 35 cycles of 94° C. for 1 min, 62° C. for 1 min, and 72° C. for 2 min (+14 extra seconds/cycle). A final elongation was done at 72° C. for 7 min. Amplification reactions were carried out using a GeneAmp 9700 PCR Systems Thermocycler (Applied Biosystems, Foster City, Calif.).

Amplification of human genomic DNA by primer extension preamplification (PEP; Zhang et al., *Proc Natl Acad Sci USA.* 89:5847–5851 (1992)) was carried out as follows. Human genomic DNA (ranging from 300 ng to 0.03 ng) was placed into 0.2 ml tubes in a total volume of 60 μl, yielding final concentrations of 33 uM PEP random primer (5'-NNN NNN NNN NNN NNN-3'), 100 uM dNTPs, 10 mM Tris-HCl, pH 8.3 (20° C.), 1.5 mM $MgCl_2$, 50 mM KCl, and 5 units of Taq DNA Polymerase (Invitrogen Life Technologies, Carlsbad, Calif.). Radioactively labeled α-$[^{32}P]$ dCTP, approximately 60 cpm/pmol total dNTPs was added to the reaction for quantitation of PCR product yield as described for MDA product quantitation in Example 3. The PEP reaction was performed for 50 cycles at 92° C. for 1 min, 37° C. for 2 min, ramping up to 55° C. at 10 sec/degree, and elongation at 55° C. for 4 min. PEP reactions were carried out using a GeneAmp 9700 PCR Systems Thermocycler (Applied Biosystems, Foster City, Calif.).

TaqMan® quantitative PCR analysis was performed as described in Example 5, and maximum amplification bias between loci was calculated by dividing the high locus representation value by the low value for each level of fold amplification. The results are shown in FIG. 6.

Figure 6:
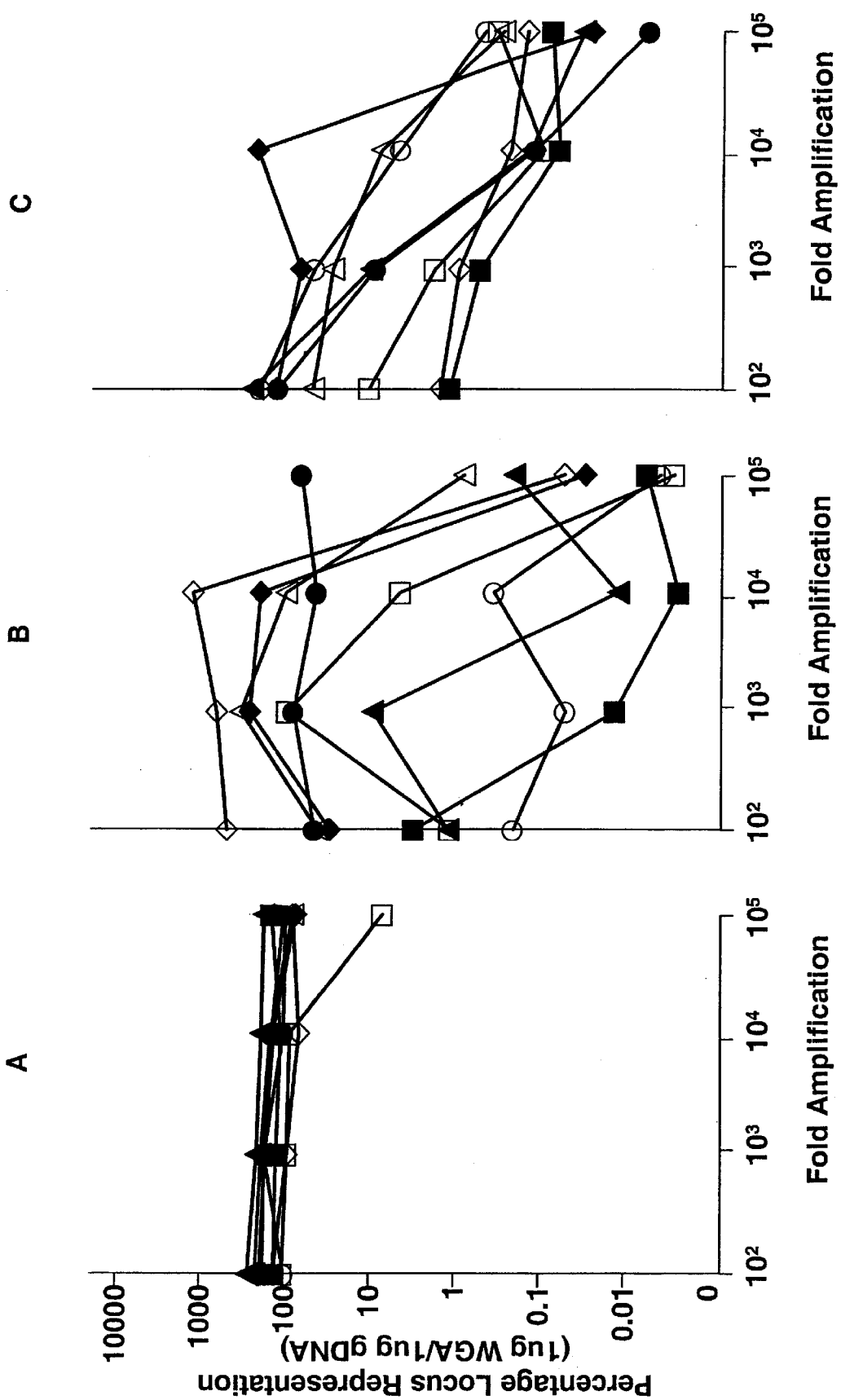
FIGS. 6A, 6B, and 6C are graphs showing the effect of amplification on gene representation bias for three different amplification procedures, MDA, DOP-PCR, and PEP.

The relative representation of eight loci is depicted in FIG. 6 for amplification reactions carried out by three different WGA procedures. The X-axis represents the fold amplification in the amplified DNA used as template for quantitative PCR; the Y-axis is the locus representation, expressed as a percent, relative to input genomic DNA, which is calculated as the yield of quantitative PCR product from 1 μg amplified DNA divided by the yield from 1 μg genomic DNA control. The results for eight loci are indicated as follows; CXCR5, open diamonds; connexin40, open triangles; MKP1, open squares; CCR6, open circles; acidic ribosomal protein, filled diamonds; CCR1, filled triangles; cJUN, filled squares; CCR7, filled circles. FIG. 6A depicts the percent representation for eight loci derived from MDA-amplified DNA. FIG. 6B depicts the percent representation for eight loci present in DNA amplified using DOP-PCR. FIG. 6C depicts the percent representation for eight loci present in PEP-amplified DNA.

As can be seen, for 100-, 1,000-, and 10,000-fold amplified MDA, the maximum amplification biases were only 2.7, 2.3, and 2.8 respectively, expressed as the ratio of the most highly represented gene to the least represented gene. Significantly, the 3-fold amplification bias of MDA remained almost constant between 100- and 100,000-fold amplification (FIG. 6A). In contrast, amplification by the DOP-PCR method exhibited an amplification bias ranging between 4 and 6 orders of magnitude (FIG. 6B). In addition, the PEP method exhibited an amplification bias spanning 2–4 orders of magnitude (FIG. 6C).

K. Example 7

Amplification Using Nested Primers Yields Specific Amplification of c-jun Sequences This example demonstrates the amplification of a specific DNA region from a complex mixture of DNA sequences using φ29 DNA polymerase with sequence-specific, nested primers.

Amplification reactions were carried out either with or without a heat denaturing/annealing step using either exonuclease-resistant hexamers or a nested set of 19 exonuclease-resistant sequence-specific primers. The nested primers used in this example are listed in Table 2. The presence of an asterisk in the nucleotide sequence indicates the presence of a phosphorothioate bond. The nested primers are designed to hybridize to opposite strands on each side of the human c-jun gene, and the closest left and right primers encompass a 3420 bp fragment containing the c-jun gene. On each side of the c-jun gene, these nested primers are spaced 150–400 nucleotides between each other. The region of human DNA encompassing the recognition sites for these primers can be accessed from Genbank using Accession Number AL136985 and spans positions 65001 to 73010 of the nucleotide sequence.

TABLE 2

Left Primers (5' to 3')

| | | | | | | | |
|---|---|---|---|---|---|---|---|
| c-Jun L9 | TCC | ATC | ACG | AGT | TAT | GC*A* C | (SEQ ID NO:1) |
| c-Jun L8 | TGG | AGT | TAC | TAA | GGG | AA*G* C | (SEQ ID NO:2) |
| c-Jun L7 | ACT | GAG | TTC | ATG | AAC | CC*T* C | (SEQ ID NO:3) |
| c-Jun L6 | ATT | AAC | TCA | TTG | AAG | GC*C* C | (SEQ ID NO:4) |
| c-Jun L5 | TCT | GTG | CTG | TAC | TGT | TG*T* C | (SEQ ID NO:5) |
| c-Jun L4 | AGT | TTG | GCA | AAC | TGG | GC*T* C | (SEQ ID NO:6) |
| c-Jun L3 | TGG | CTC | TTG | GTA | TGA | AA*A* G | (SEQ ID NO:7) |
| c-Jun L2 | ACT | GTT | AGT | TTC | CAT | AG*G* C | (SEQ ID NO:8) |
| c-Jun L1 | TGA | ATA | CAT | TTA | TTG | TG*A* C | (SEQ ID NO:9) |

TABLE 2-continued

Right Primers (5' to 3')

| | | | | | | | |
|---|---|---|---|---|---|---|---|
| c-Jun R1 | CGA | CTG | TAG | GAG | GGC | AG*C* G | (SEQ ID NO:10) |
| c-Jun R2 | CGT | CAG | CCC | ACA | ATG | CA*C* C | (SEQ ID NO:11) |
| c-Jun R3 | GTA | CTT | GGA | TTC | TCA | GC*C* T | (SEQ ID NO:12) |
| c-Jun R4 | CAA | ATC | TCT | CGG | CTT | CT*A* C | (SEQ ID NO:13) |
| c-Jun R5 | CGT | GTT | GTG | TTA | AGC | GT*G* T | (SEQ ID NO:14) |
| c-Jun R6 | CCG | CGG | AAA | AGG | AAC | CA*C* T | (SEQ ID NO:15) |
| c-Jun R7 | CTC | CTG | GCA | GCC | CAG | TG*A* G | (SEQ ID NO:16) |
| c-Jun R8 | CTC | CTC | CCC | TCG | ATG | CT*T* C | (SEQ ID NO:17) |
| c-Jun R9 | CAG | TTA | CCC | TCT | GCA | GA*T* C | (SEQ ID NO:18) |
| c-Jun R10 | CTA | TTT | CCT | CTG | CAG | AT*A* A | (SEQ ID NO:19) |

Figure 7:
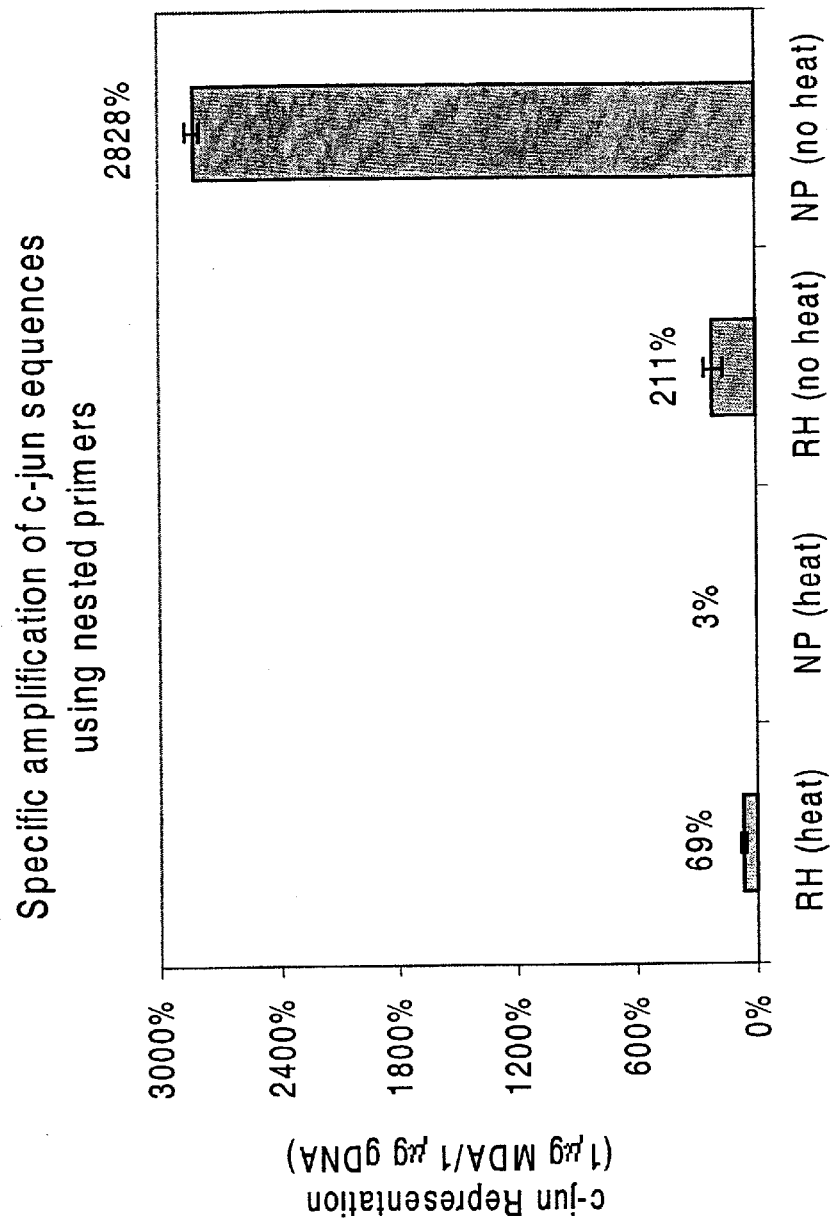
FIG. 7 is a graph showing amplification of c-jun sequences using nested primers.

Four reactions were carried out under the following conditions. Human genomic DNA (50 ng) was placed into a 0.2 ml tube in a total volume of 50 µl, yielding final concentrations of 25 mM Tris-HCl, pH 7.5, 50 mM KCl, 10 mM MgCl$_2$, and 100 µM exonuclease-resistant hexamer or 1 µM each of exonuclease-resistant nested primers. A heat-treatment step to increase primer annealing was included or omitted, as indicated, for individual reactions. Annealing reactions were heated to 95° C. for 3 minutes and slowly cooled down to 37° C. in a PCR System Thermocycler (Perkin Elmer). Reactions were divided into two, each had 25 µl and then was brought to a final volume of 50 µl, containing final concentrations of 37 mM Tris-HCl, pH 8.0, 50 mM KCl, 10 mM MgCl$_2$, 5 mM (NH$_4$)$_2$SO$_4$, 1.0 mM dNTPs, 1 unit/ml of yeast pyrophosphatase, 50 µM exonuclease-resistant hexamer or 0.5 µM exonuclease-resistant nested primers, and 800 units/ml φ29 DNA polymerase. Radioactively labeled α-[$^{32}$P] dCTP, approximately 60 cpm/pmol total dNTPs, was added to one of two parallel reactions for quantification of DNA synthesis. Reactions were incubated for 18 hours at 37° C. Incorporation of acid-precipitable radioactive deoxyribonucleotide product was determined with glass fiber filters. The reactions that did not contain α-[$^{32}$P] dCTP were analyzed by TaqMan® quantitative PCR analysis as described in Example 5. A standard curve for input template was generated to determine the locus copy number of the amplified DNA sample relative to that of genomic DNA. The standard curve was generated from 0, 0.001, 0.01, 0.1, 0.5, and 1 µg of genomic DNA. The results are shown in FIG. 7.

The Y-axis is the locus representation relative to input genomic DNA. It is calculated as the yield of quantitative PCR product from 1 µg amplified DNA divided by the yield from 1 µg genomic DNA control, expressed as a percent.

As can be seen, the representation of c-jun sequences amplified with random hexamers from DNA heated to 95° C. was 69% (see RH (heat) bar). The representation of c-jun sequences amplified with nested primers from DNA heated to 95° C. was only 3% (see NP (heat) bar). The representation of c-jun sequences in DNA amplified with random hexamers without template DNA heat treatment was 211% (see RH (no heat) bar). The representation of c-jun sequences in DNA amplified with nested primers without template DNA heat treatment was 2828% (see NP (no heat) bar).

L. Example 8

Amplification Bias of Loci Amplified by MDA from Whole Blood

This example demonstrates that genomic DNA can be amplified using MDA directly from whole blood or from tissue culture cells and that the locus representation is substantially the same as for DNA amplified from purified genomic DNA template. As a control, DNA amplified in the absence of added template was tested and contains no detectable sequence representation for these loci.

DNA was prepared from blood or a tissue culture cell line as follows. Human blood samples were obtained from Grove Hill Laboratory. U266, a myeloma cell line, was obtained from ATCC and passaged according to the accompanying protocol. Cells were lysed in an alkaline lysis solution by a modification of Zhang et al. (Zhang, L. et al. Whole genome amplification from a single cell: implications for genetic analysis. *Proc Natl Acad Sci USA*. 89, 5847–5851 (1992)). Blood was diluted 3-fold in PBS (137 mM NaCl, 2.7 mM KCl, 9.5 mM Na, $KPO_4$, pH 7.4), while tissue culture cells were diluted to 30,000 cells/ml in PBS. Blood or cells were lysed by dilution with an equal volume of Alkaline Lysis Buffer (400 mM KOH, 100 mM dithithreitol, and 10 mM EDTA) and incubated 10 min on ice. The lysed cells were neutralized with the same volume of Neutralization Buffer (400 mM HCl, 600 mM Tris-HCl, pH 7.5). Preparations of lysed blood or cells (1 µl) were used directly as template in MDA reactions (100 µg) as described.

MDA reactions (100 µl) were carried out without denaturation at 95° C. as described in Example 5. Reactions using purified human genomic DNA template contained 300 or 30 ng DNA, resulting in approximately 100- or 1000-fold DNA amplification. Reactions using DNA from lysed blood or cells contained 1 µl of the neutralized cell lysates as template. Control amplification reactions contained no added template DNA.

Figure 8:
FIG. 8 is a graph the relative representation of eight loci for DNA from five different amplification reactions. The Y-axis is the locus representation, expressed as a percent, relative to input genomic DNA, which is calculated as the yield of quantitative PCR product from 1 μg of amplified DNA divided by the yield from 1 μg of genomic DNA control.

TaqMan® quantitative PCR analysis was performed on amplified DNA samples as described in Example 5, and the results are shown in FIG. 8. The relative representation of eight loci for DNA from five different amplification reactions is depicted in FIG. 8. The Y-axis is the locus representation, expressed as a percent, relative to input genomic DNA, which is calculated as the yield of quantitative PCR product from 1 µg of amplified DNA divided by the yield from 1 µg of genomic DNA control. Bars with declining diagonals depict the locus representation for DNA amplified from whole blood. Solid gray bars depict the locus representation for DNA amplified from 30 ng purified genomic DNA (9,000 genome copies). Solid white bars depict the locus representation for DNA amplified from 300 ng purified genomic DNA (90,000 genome copies). Bars with rising diagonals depict the locus representation for DNA amplified from tissue culture cells (10 cell equivalents of DNA). Solid black bars depict the locus representation for DNA amplified from reactions with no added template (the values for the data represented by the black bars are so small that the bars are not visible on the graph).

As can be seen, DNA amplified directly from whole blood or from tissue culture cells has substantially the same values for locus representation as DNA amplified from purified genomic DNA template.

M. Example 9

The Amplification Bias of Loci Amplified by MDA in Reactions Containing AAdUTP is the Same as the Amplification Bias of DNA Amplified in Reactions Containing 100% dTTP This example demonstrates that genomic DNA can be amplified using MDA in reactions containing AAdUTP (5-(3-aminoallyl)-2'-deoxyuridine 5'-triphosphate, Sigma-Aldrich Co.) and that the locus representation is substantially the same as for DNA amplified in reactions containing only dTTP.

MDA reactions (100 µl) containing 100% dTTP were carried out without denaturation at 95° C. as described in Example 5. Reactions containing 70% AAdUTP were carried out under the same conditions as reactions containing 100% dTTP, with the exception that they contained 0.7 mM AAdUTP and 0.3 mM dTTP, instead of the standard 1.0 mM dTTP. Reactions contained 1 ng human genomic DNA template, resulting in approximately 30,000-fold DNA amplification.

Figure 9:
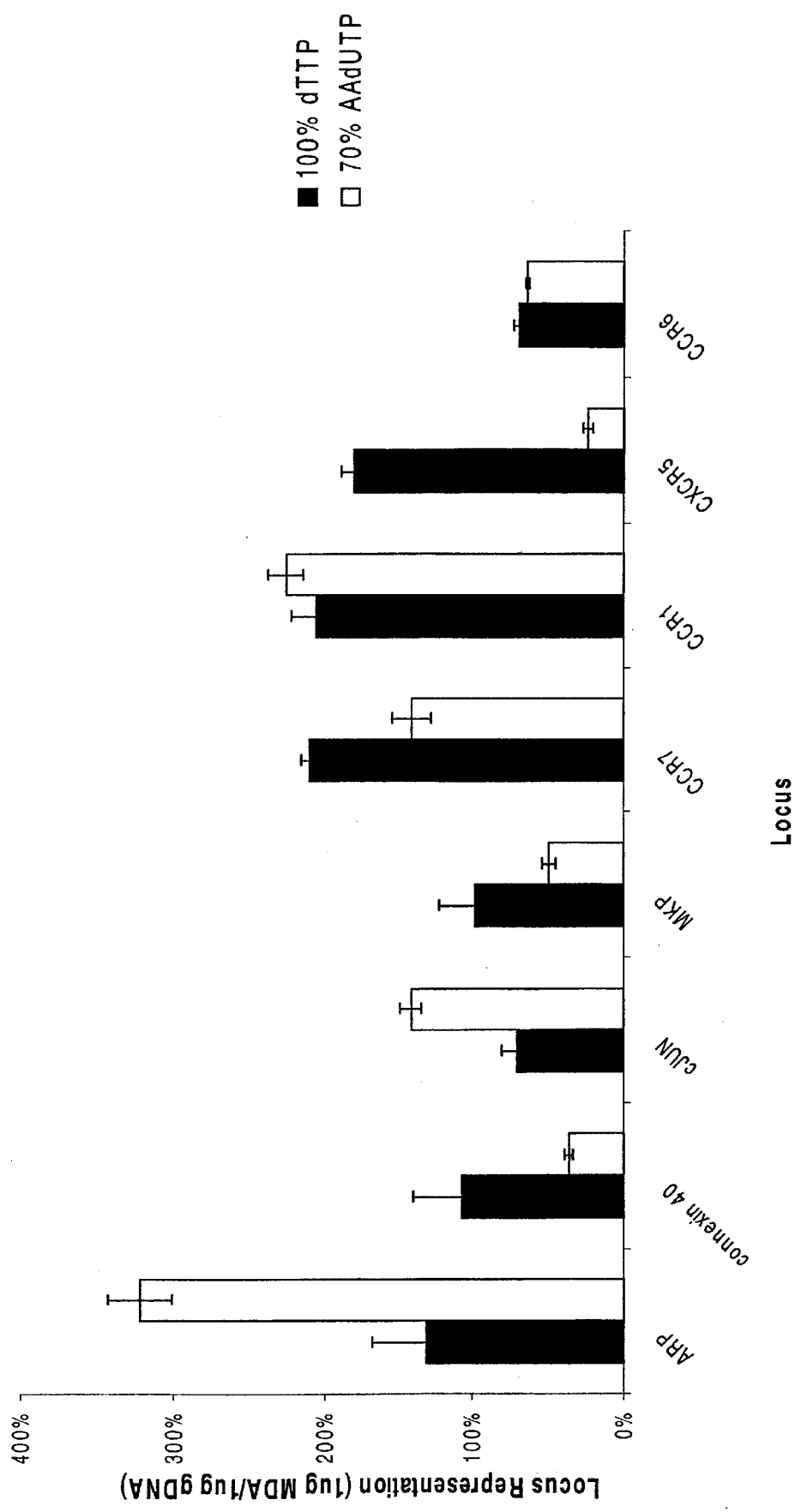
FIG. 9 is a graph showing a comparison of the percent representation for 8 loci for DNA amplified in a reaction containing 100% dTTP and DNA amplified in a reaction containing 30% dTTP/70% AAdUTP.

TaqMan® quantitative PCR analysis was performed on amplified DNA samples as described in Example 5, and the relative representation of eight loci for DNA from two amplification reactions is depicted in FIG. 9. The Y-axis is the locus representation, expressed as a percent, relative to input genomic DNA, which is calculated as the yield of quantitative PCR product from 1 µg of amplified DNA divided by the yield from 1 µg of genomic DNA control. Black bars depict the locus representation for DNA amplified in a reaction containing 100% dTTP. White bars depict the locus representation for DNA amplified in a reaction containing 30% dTTP/70% AAdUTP.

As can be seen, DNA amplified in reactions containing 30% dTTP/70% AAdUTP has substantially the same values for locus representation as DNA amplified in reactions containing 100% dTTP.

N. Example 10

Amplification of c-jun Sequences from Human Genomic DNA Using Sequence Specific Primers and Target Circularization This example describes an embodiment of the disclosed method and analysis of the resulting DNA products. The exemplified method is the disclosed gene-specific multiple displacement amplification form of multiple strand displacement amplification using nuclease-resistant sequence-specific primers and circularized DNA template.

Amplification reactions were carried out without a heat denaturing/annealing step under the conditions described in Example 5 using exonuclease-resistant sequence-specific primers that hybridize to sequences within a 5.5 kb EcoRI fragment that contains the c-jun sequence. The sequence-specific primers used in this example are listed in Table 3. An asterisk in the nucleotide sequence indicates the presence of a phosphorothioate bond. The sequence-specific primers are designed to hybridize to opposite strands on each side of the c-jun gene sequence, and the primers encompass a 2025 bp fragment containing the c-jun gene sequence. The primers are spaced 150–400 nucleotides between each other on each side of the c-jun gene sequence. The region of human DNA encompassing the recognition sites for these primers can be accessed from Genbank using Accession Number AL136985 and spans positions 66962 to 68987 of the nucleotide sequence.

TABLE 3

Left Primers (5' to 3')

| | | |
|---|---|---|
| c-Jun D1 | CTG AAA CAT CGC ACT AT*C *C | (SEQ ID NO:21) |
| c-Jun D2 | CCA AAC TTT GAA ATG TT*T *G | (SEQ ID NO:22) |
| c-Jun D3 | CTG CCA CCA ATT CCT GC*T *T | (SEQ ID NO:23) |

TABLE 3-continued

| | | | | | | | | |
|---|---|---|---|---|---|---|---|---|
| c-Jun D4 | CAT | AAG | CAA | AGG | CCA | TC*T | *T | (SEQ ID NO:24) |
| c-Jun D5 | GGA | AGC | AAT | TCA | AGA | TC*T | *G | (SEQ ID NO:25) |
| c-Jun D6 | CTT | CAG | ATT | GCA | GCA | AT*G | *T | (SEQ ID NO:26) |
| c-Jun D7 | GAA | TTA | ATG | AAA | TTG | GG*A | *G | (SEQ ID NO:27) |
| c-Jun D8 | ACT | GTT | AGT | TTC | CAT | AG*G | *C | (SEQ ID NO:28) |
| c-Jun D9 | CAA | GGT | TGA | TTA | TTT | TA*G | *A | (SEQ ID NO:29) |
| c-Jun D10 | AGT | ACT | AGT | TCA | TGT | TT*T | *C | (SEQ ID NO:30) |
| Right Primers (5' to 3') | | | | | | | | |
| c-Jun U1 | TAG | TAC | TCC | TTA | AGA | AC*A | *C | (SEQ ID NO:31) |
| c-Jun U2 | CTA | ACA | TTC | GAT | CTC | AT*T | *C | (SEQ ID NO:32) |
| c-Jun U3 | GCG | GAC | GGG | CTG | TCC | CC*G | *C | (SEQ ID NO:33) |
| c-Jun U4 | GGA | AGG | ACT | TGG | CGC | GC*C | *C | (SEQ ID NO:34) |
| c-Jun U5 | AAC | TAA | AGC | CAA | GGG | TA*T | *C | (SEQ ID NO:35) |
| c-Jun U6 | ATA | ACA | CAG | AGA | GAC | A*G | *A | (SEQ ID NO:36) |
| c-Jun U7 | CAA | CTC | ATG | CTA | ACG | CA*G | *C | (SEQ ID NO:37) |
| c-Jun U8 | GGA | AGC | TGG | AGA | GAA | TC*G | *C | (SEQ ID NO:38) |
| c-Jun U9 | GAC | ATG | GAG | TCC | CAG | GA*G | *C | (SEQ ID NO:39) |
| c-Jun U10 | AGG | CCC | TGA | AGG | AGG | AG*C | *C | (SEQ ID NO:40) |

Figure 10:
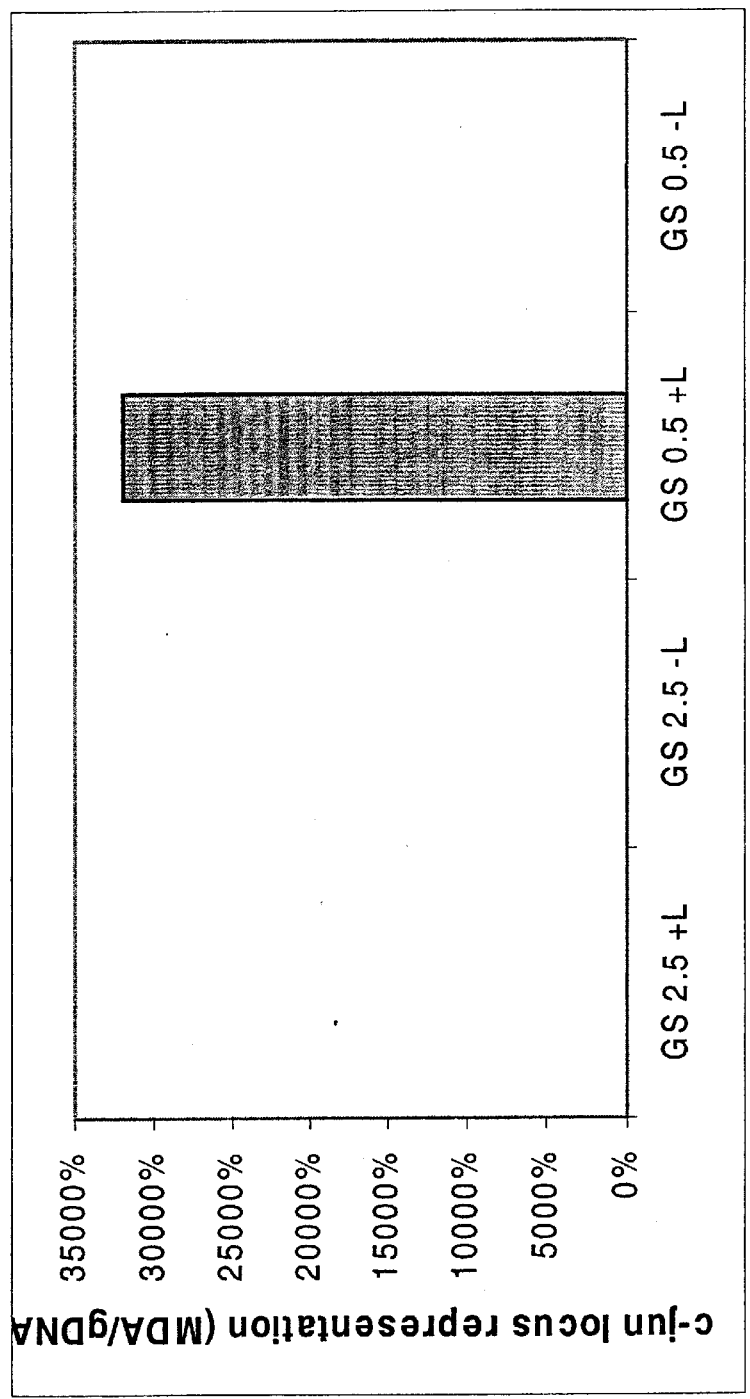
FIG. 10 is a graph showing the amplification of c-jun sequences using circularized genomic template. The Y-axis is the locus representation, expressed as a percent, relative to input genomic DNA, which is calculated as the yield of quantitative PCR product from 1 μg of amplified DNA divided by the yield from 1 μg of genomic DNA control.

Four reactions were carried out under the following conditions. Human genomic DNA (5 µg, Coriell Cell Repositories) was digested with 100 units of EcoRI for 3 hours in 50 µl according to the manufacturers conditions. The EcoRI endonuclease was inactivated by incubation at 65° C. for 30 min. Digested DNA fragments (0.5 µg) were circularized in an 840 µl volume using 1.7 units (Weiss units) of T4 DNA ligase. The reaction was incubated for 16 h at 4° C. A mock ligation was carried out under identical conditions except for the omission of DNA ligase. Two amplification reactions utilizing a portion of the ligated mixture as template (16.8 µl; 10 ng DNA) were carried out, one with sequence-specific primers at a concentration of 2.5 µM each and the other with the primers at a concentration of 0.5 µM each. Two more amplification reactions were carried out utilizing the mock-ligated DNA as template with sequence-specific primer concentrations of 2.5 µM and 0.5 µM. Radioactively labeled α-[$^{32}$P] dCTP, approximately 60 cpm/pmol total dNTPs, was added to parallel reactions for quantification of DNA synthesis. Reactions were incubated for 18 hours at 37° C. The reactions that did not contain α-[$^{-}$P] dCTP were analyzed by TaqMan® quantitative PCR analysis as described in Example 5. A standard curve for input template was generated to determine the locus copy number of the amplified DNA sample relative to that of genomic DNA. The standard curve was generated from 0, 0.001, 0.01, 0.1, 0.5, and 1 µg of genomic DNA. The results are shown in FIG. 10. The Y-axis is the locus representation relative to input genomic DNA. It is calculated as the yield of quantitative PCR product from 1 µg amplified DNA divided by the yield from 1 µg genomic DNA control, expressed as a percent.

As can be seen, the representation of c-jun sequences amplified with 2.5 µM Gene-Specific primers from ligated DNA was below detection (see GS 2.5+L bar). The representation of c-jun sequences amplified with 2.5 µM Gene-Specific primers from mock-ligated DNA was also not detected (see GS 2.5–L bar). The representation of c-jun sequences in DNA amplified with 0.5 µM Gene-Specific primers from ligated DNA was 32000% (see GS 0.5+L bar). The representation of c-jun sequences in DNA amplified with 0.5 µM Gene-Specific primers from mock-ligated DNA was also not detected (see GS 0.5–L bar). These results demonstrate a 320-fold amplification of the c-jun sequences using gene-specific primers and circularized template DNA. Digested DNA that was not ligated did not show any appreciable amplification. Only ligated DNA that was amplified with 0.5 µM primers was amplified, while 2.5 µM primers did not yield any amplification.

Figure 11:
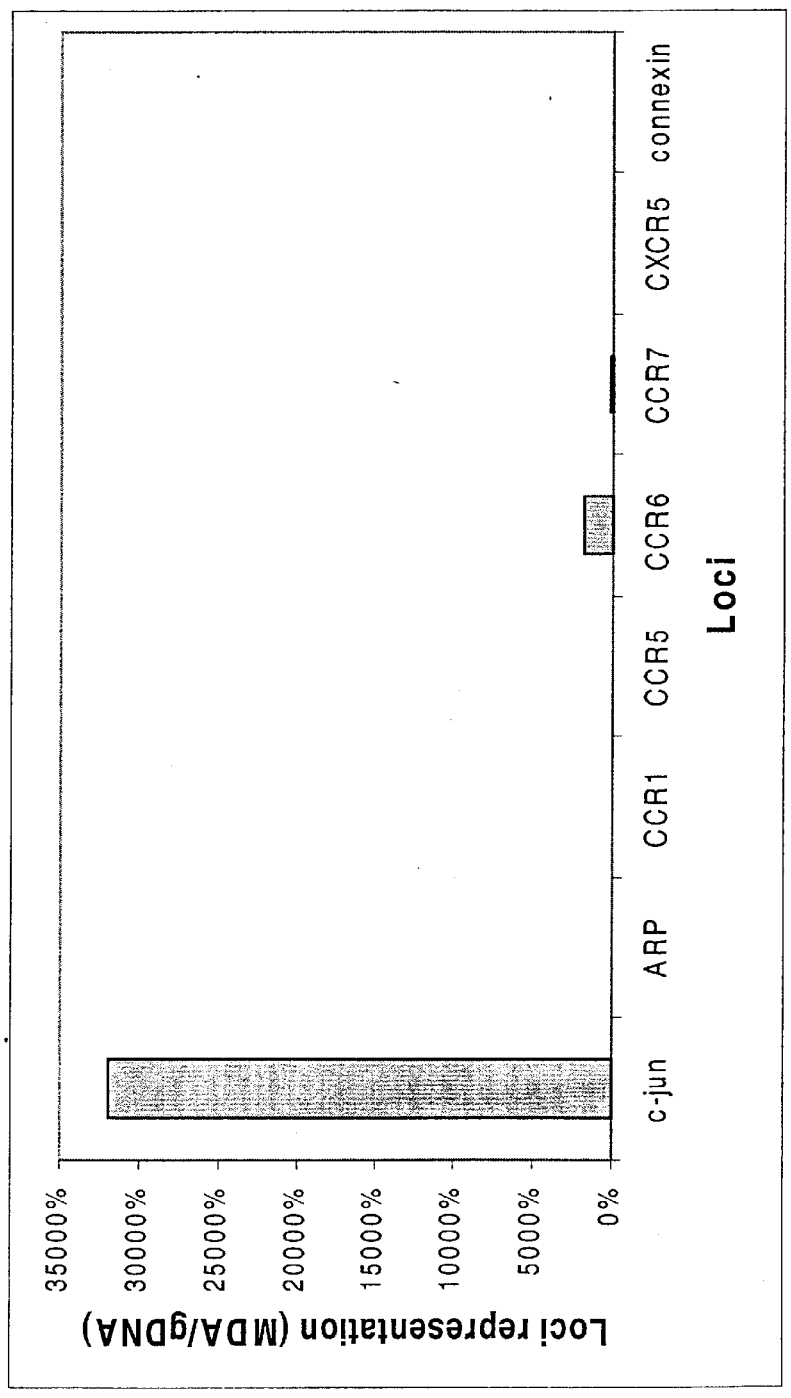
FIG. 11 is a graph showing a comparison of the percent representation for 8 loci in DNA amplified using c-jun specific primers and circularized DNA target.

The specificity of the DNA amplification reaction carried out with 2.5 µM Gene-Specific primers and circularized DNA template was tested by comparing it to the amount of DNA amplification observed at seven other loci. TaqMan® quantitative PCR analysis was performed as described in Example 5, and the results are shown in FIG. 11. The relative representation of the c-jun locus and seven other loci is depicted and the seven loci showed only low levels of amplification, indicating that the c-jun sequences were specifically amplified using the c-jun specific primers.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a ", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A method of amplifying a whole genome, the method comprising, bringing into contact a set of primers, DNA polymerase, and a target sample, wherein the target sample comprises a whole genome, and incubating the target sample under conditions that promote replication of the genome, wherein the target sample is not subjected to denaturing conditions, wherein replication of the genome results in replicated strands, wherein during replication at least one of the replicated strands is displaced from the genome by strand displacement replication of another replicated strand.

2. The method of claim 1 wherein the primers are 6 nucleotides long, wherein the primers each contain at least one modified nucleotide such that the primers are nuclease resistant, and wherein the DNA polymerase is φ29 DNA polymerase.

3. The method of claim 1 wherein the primers are of random nucleotide composition, wherein the primers each contain at least one modified nucleotide such that the primers are nuclease resistant, and wherein the DNA polymerase is φ29 DNA polymerase.

4. A method of amplifying a chromosome, the method comprising, bringing into contact a set of primers, DNA polymerase, and a target sample, wherein the target sample comprises a chromosome, and incubating the target sample under conditions that promote replication of the chromsome, wherein the target sample is not subjected to denaturing conditions, wherein replication of the chromosome results in replicated strands, wherein during replication at least one of the replicated strands is displaced from the chromosome by strand displacement replication of another replicated strand.

5. The method of claim 4 wherein the primers are 6 nucleotides long, wherein the primers each contain at least one modified nucleotide such that the primers are nuclease resistant, and wherein the DNA polymerase is φ29 DNA polymerase.

6. The method of claim 4 wherein the primers are of random nucleotide composition, wherein the primers each contain at least one modified nucleotide such that the primers are nuclease resistant, and wherein the DNA polymerase is φ29 DNA polymerase.

* * * * *

SEQUENCE LISTING

<160> NUMBER OF SEQ ID NOS: 40

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 1
tccatcacga gttatgcac                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 2
tggagttact aagggaagc                                                    19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 3
actgagttca tgaaccctc                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 4
attaactcat tgaaggccc                                                    19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 5
tctgtgctgt actgttgtc                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 6
agtttggcaa actgggctc                                    19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 7
tggctcttgg tatgaaaag                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 8
actgttagtt tccataggc                                    19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 9
tgaatacatt tattgtgac                                    19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 10
cgactgtagg agggcagcg                                    19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 11
cgtcagccca caatgcacc                                    19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 12
gtacttggat tctcagcct                                              19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 13
caaatctctc ggcttctac                                              19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 14
cgtgttgtgt taagcgtgt                                              19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 15
ccgcggaaaa ggaaccact                                              19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 16
ctcctggcag cccagtgag                                              19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 17
ctcctcccct cgatgcttc                                              19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 18
cagttaccct ctgcagatc                                                19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 19
ctatttcctc tgcagataa                                                19

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence; Note =
      synthetic construct
<221> NAME/KEY: misc_feature
<222> LOCATION: 11-16
<223> OTHER INFORMATION: N = a, g, c, or t (u)

<400> SEQUENCE: 20
ccgactcgag nnnnnnatgt gg                                            22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 21
ctgaaacatc gcactatcc                                                19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 22
ccaaactttg aaatgtttg                                                19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 23
ctgccaccaa ttcctgctt                                                19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

```
<400> SEQUENCE: 24
cataagcaaa ggccatctt                                           19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 25
ggaagcaatt caagatctg                                           19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 26
cttcagattg cagcaatgt                                           19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 27
gaattaatga aattgggag                                           19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 28
actgttagtt tccataggc                                           19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 29
caaggttgat tattttaga                                           19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 30
```
agtactagtt catgttttc                                              19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 31
tagtactcct taagaacac                                              19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 32
ctaacattcg atctcattc                                              19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 33
gcggacgggc tgtccccgc                                              19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 34
ggaaggactt ggcgcgccc                                              19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 35
aactaaagcc aagggtatc                                              19

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 36

-continued

```
ataacacaga gagacaga                                                       18

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 37
caactcatgc taacgcagc                                                      19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 38
ggaagctgga gagaatcgc                                                      19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 39
gacatggagt cccaggagc                                                      19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 40
aggccctgaa ggaggagcc                                                      19
```